(12) United States Patent
Helleday et al.

(10) Patent No.: US 7,531,530 B2
(45) Date of Patent: *May 12, 2009

(54) THERAPEUTIC COMPOUNDS

(75) Inventors: Thomas Helleday, Stockholm (SE); Nicola Curtin, Tyne and Wear (GB)

(73) Assignees: Cancer Research Technology Limited, London (GB); Pfizer, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/565,308

(22) PCT Filed: Jul. 23, 2004

(86) PCT No.: PCT/GB2004/003183

§ 371 (c)(1),
(2), (4) Date: Mar. 27, 2006

(87) PCT Pub. No.: WO2005/012305

PCT Pub. Date: Feb. 10, 2005

(65) Prior Publication Data

US 2007/0072841 A1    Mar. 29, 2007

(30) Foreign Application Priority Data

Jul. 25, 2003   (GB)   .................................. 0317466.1
Apr. 16, 2004   (GB)   .................................. 0408524.7

(51) Int. Cl.
*A61P 35/00* (2006.01)

(52) U.S. Cl. .................................. 514/212.06; 514/220

(58) Field of Classification Search ................ 540/498, 540/520; 514/212.06, 220
See application file for complete search history.

(56) References Cited

U.S. PATENT DOCUMENTS

| | | | |
|---|---|---|---|
| 6,495,541 B1 | 12/2002 | Webber et al. | |
| 6,548,494 B1 | 4/2003 | Webber et al. | |
| 2005/0059663 A1 | 3/2005 | Martin et al. | |
| 2005/0227919 A1 | 10/2005 | Ashworth et al. | |
| 2006/0074073 A1 | 4/2006 | Steinfeldt et al. | |

FOREIGN PATENT DOCUMENTS

| | | |
|---|---|---|
| WO | 0042040 A1 | 7/2000 |
| WO | 0116136 A2 | 3/2001 |
| WO | 2004087713 A1 | 10/2004 |
| WO | 2005012524 A1 | 2/2005 |

OTHER PUBLICATIONS

Bryant, et al., Specific killing of BRCA2-deficient tumours with inhibitors of poly(ADP-ribose) polymerase, Nature, Apr. 14, 2005, 913-917, vol. 434.
Canan Koch, et al., Novel Tricyclic Poly(ADP-ribose) Polymerase-1 Inhibitors with Potent Anticancer Chemopotentiating Activity: Design, Synthesis, and X-ray Cocrystal Structure, J. Med. Chem., 2002, 4961-4974, vol. 45, No. 23.
Easton, et al., Cancer Risks in BRCA2 Mutation Carriers, J. Natl. Cancer Inst., 1999, 1310-1316, vol. 91, No. 15.
Farmer, et al., Targeting the DNA repair defect in BRCA mutant cells as a therapeutic strategy, Nature, Apr. 14, 2005, 917-921, vol. 434.
Friedenson, et al., BRCA1 and BRCA2 Pathways and the Risk of Cancers Other Than Breast or Ovarian, Medscape General Medicine, 2005, 7(2):60.
Lakhani, et al., The Pathology of Familial Breast Cancer: Predictive Value of Immunohistochemical Markers Estrogen Receptor, Progesterone Receptor, HER-2, and p53 in Patients With Mutations in BRCA1 and BRCA2, Journal of Clinical Oncology, May 1, 2002, 2310-2318, vol. 20, No. 9.
Quinn, et al., BRCA1 Functions as a Different Modulator of Chemotherapy-induced Apoptosis, Cancer Research, Oct. 1, 2003, 6221-6228, vol. 63.
Taron, et al., BRCA1 mRNA expression levels as an indicator of chemoresistance in lung cancer, Human Molecular Genetics, 2004, 2443-2449, vol. 13, No. 20.
Tutt, et al., The relationship between the roles of BRCA genes in DNA repair and cancer predisposition, Trends in Molecular Medicine, Dec. 2002, 571-576, vol. 8, No. 12.
Venkitaraman, A. R., Cancer Susceptibility and the Functions of BRCA1 and BRCA2, Cell, Jan. 25, 2002, 171-182, vol. 108.
PCT International Search Report for PCT/GB2004/003183 (WO 2005/012305).
PCT Written Opinion of the International Searching Authority for PCT/GB2004/003183 (WO 2005/012305).

*Primary Examiner*—Bruck Kifle
(74) *Attorney, Agent, or Firm*—Notaro & Michalos P.C.

(57) ABSTRACT

The invention relates to trycyclic lactam indole derivatives and triacyclic lactam benzimodole derivatives and their use in inhibiting the activity of PARP enzyme. The invention also relates to the use of these compounds in the preparation of medicaments.

15 Claims, 8 Drawing Sheets

THERAPEUTIC COMPOUNDS

This invention relates to a series of compounds derived which are derivatives of tricyclic lactam indoles and tricyclic lactam benzimidazoles and which inhibit poly (ADP-ribose) polymerase (PARP) and their use in the treatment of cancer, in particular breast cancer.

Homologous recombination (HR) has been shown to play an important role in repair of damage occurring at DNA replication forks in mammalian cells (2). Thus, cells deficient in HR show retarded growth and exhibit higher levels of genetic instability. It is believed that genetic instability due to loss of HR repair in human cancers significantly contributes to the development of cancer in these cells (1).

Post transcriptional modification of nuclear proteins by poly (ADP-ribosyl)ation in response to DNA strand breaks plays an important role in DNA repair, regulation of apoptosis, and maintenance of genomic stability.

Poly (ADP-ribose) polymerase (PARP-1) is the principal member of the PARP enzyme family and is an abundant nuclear protein in mammalian cells. PARP-1 catalyses the formation of poly (ADP-ribose) (PAR) polymers using $NAD^+$ as substrate. Upon DNA damage, PARP-1 binds rapidly to a DNA single-strand break (SSB) and catalyses the addition of negatively charged PAR chains to itself (auto-modification) and other proteins [see (3, 4) for reviews]. The binding of PARP-1 to SSBs is believed to protect DNA lesions from further processing until PARP-1 is dissociated from the break by the accumulated negative charge resulting from PAR polymers (5, 6).

Although PARP-1 has been implicated in several nuclear processes, such as modulation of chromatin structure, DNA-replication, DNA repair and transcription, PARP-1 knockout mice develop normally (7). Cells isolated from these mice exhibit a hyper recombination phenotype and genetic instability in the form of increased levels of sister chromatic exchanges (SCE) micronuclei and tetraploidy (8, 10). Genetic instability may also occur in these PARP-1 knockout mice through telomere shortening, increased frequency of chromosome fusion and aneuploid (11), although all these results could not be repeated in another set of PARP-1 knockout mice (12). In the former mice knockout, PARP-1 null mutation rescued impaired V(D)J recombination in SCID mice (13).

These results support the view suggested by Lindahl and co-workers that PARP-1 has a protective role against recombination (5). It was proposed that binding of PARP-1 to ssDNA breaks prevents the recombination machinery from recognising and processing DNA lesions or, alternatively that the negative charges accumulated following poly (ADP-ribosyl)ation repel adjacent recombinogenic DNA sequences. Only the latter model is consistent with inhibition of PARP-1 itself and expression of a dominant negative mutant PARP-1, including SCE, gene amplification and homologous recombination (14-18).

Studies based on treating cells with inhibitors of PARP-1 or cells derived from PARP-1 knockout mice indicate that the suppression of PARP-1 activity increases cell susceptibility to DNA damaging agents and inhibits strand break rejoining (3, 4, 8-11, 19, 20).

Inhibitors of PARP-1 activity have been used in combination with traditional cancer treatment regimes such as radiotherapy and chemotherapy (21). When the inhibitors were used in combination with methylating agents, topoisomerase poisons and ionising radiations they were found to enhance the effectiveness of these forms of treatment. However, such treatments are non-selective and as such cause damage and death to non-cancerous or 'healthy' cells. Furthermore, such treatments are known to give rise to unpleasant side effects.

Therefore, it is highly desirable to provide a treatment for cancer that is both effective and selective in the killing of cancer cells and which does not need to be administered in combination with radio-therapy or chemotherapy treatments.

Surprisingly it has been found that cells deficient in homologous recombination (HR) are hypersensitive to PARP inhibitors relative to wild type cells.

Thus, according to a first aspect of the present invention there is provided a compound for inhibiting the activity of PARP having formula I:

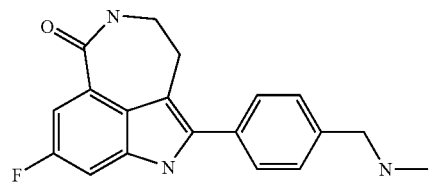

I and pharmaceutically acceptable salts thereof.

According to a second aspect of the present invention there is provided a compound for inhibiting the activity of PARP having formula II:

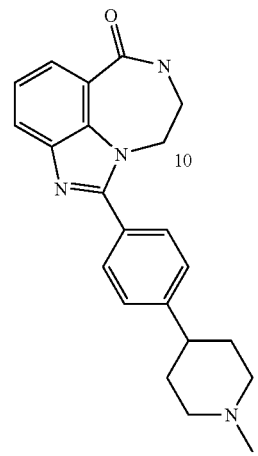

II and pharmaceutically acceptable salts thereof.

According to a third aspect of the present invention there is provided a compound for inhibiting the activity of PARP having formula III:

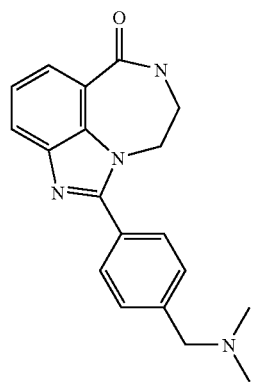

III and pharmaceutically acceptable salts thereof.

The compounds described herein can be prepared by synthetic routes based on those disclosed in WO 00/42040 and WO 01/16136.

It will be understood that where reference is made in this specification to compounds of formulas I to III the reference should be construed as extending also to their pharmaceutically acceptable salts and to other pharmaceutically acceptable bioprecursors (prodrug forms) where relevant. The term "prodrug" is used in the present specification to denote modified forms or derivatives of a pharmacologically active compound which biodegrade or are modified in vivo so as to become converted into said active compound after administration, especially oral or intravenous administration, in the course of therapeutic treatment of a mammal. Such prodrugs are commonly chosen because of an enhanced solubility in aqueous media which helps to overcome formulation problems, and also in some cases to give a relatively slow or controlled release of the active agent.

As referred to herein pharmaceutically acceptable salts include metal salts, phosphates and quaternary amines. The metal salts may be formed with alkali metals such as lithium, sodium or potassium.

Preferably, formula I, above, is administered in the form of a pharmaceutically acceptable phosphate salt having the following formula:

Formula I-phosphate

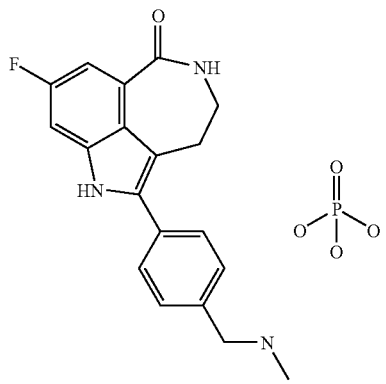

The present invention also relates to the therapeutic utility of the compounds described herein.

Thus, according to a further aspect of the present invention there is provided the use of a therapeutic amount of a compound of formula I, and pharmaceutically acceptable salts thereof, in the manufacture of a medicament.

According to a further aspect of the present invention there is provided the use of a therapeutic amount of a compound of formula II, and pharmaceutically acceptable salts thereof, in the manufacture of a medicament.

According to a further aspect of the present invention there is provided the use of a therapeutic amount of a compound of formula III, and pharmaceutically acceptable salts thereof, in the manufacture of a medicament.

According to a further aspect of the present invention there is provided the use of a therapeutic amount of a compound of formula I, and pharmaceutically acceptable salts thereof, in the manufacture of a medicament for the treatment of a disease or condition that is caused by a genetic defect in a gene that mediates homologous recombination.

According to a further aspect of the present invention there is provided the use of a compound of formula II in the manufacture of a medicament for the treatment of a disease or condition that is caused by a genetic defect in a gene that mediates homologous recombination.

According to a further aspect of the present invention there is provided the use of a compound of formula III in the manufacture of a medicament for the treatment of a disease or condition that is caused by a genetic defect in a gene that mediates homologous recombination.

Diseases and conditions which are caused by a genetic defect in a gene that mediates homologous recombination include, but are not limited to cancer, in particular breast cancer.

As referred herein "cancer" or "tumour" includes, but is not limited to, cancer of the lung, colon, pancreas, stomach, ovary, cervix, breast, prostate bone, brain or skin.

The use of PARP inhibitors is particularly suitable in the treatment of cancer which is caused by a genetic defect in a gene wherein the said gene mediates homologous recombinations. Cancer cells of this type tend to be HR defective.

The specific sensitivity of HR defective tumours to PARP inhibition means that normally dividing "healthy" cells in patients which have adequate amounts of HR will be largely unaffected by the treatment.

A further advantage of treatment using PARP inhibitors is that the PARP inhibitors do not need to be administered as a combination therapy along with conventional radiotherapy or chemotherapy treatments thereby avoiding the side effects associated with these conventional forms of treatment.

A defect in a gene that mediates homologous recombination may be due to a mutation in, the absence of, or defective expression of, a gene encoding a protein involved in HR.

According to a further aspect of the present invention there is provided the use of a therapeutic amount of a compound of formula I in the manufacture of a medicament for inducing apoptosis in HR defective cells.

According to a further aspect of the present invention there is provided the use of a therapeutic amount of a compound of formula II in the manufacture of a medicament for inducing apoptosis in HR defective cells.

According to a further aspect of the present invention there is provided the use of a therapeutic amount of a compound of formula III in the manufacture of a medicament for inducing apoptosis in HR defective cells.

According to a further aspect of the present invention there is provided the use of a therapeutic amount of a compound of formula I in the manufacture of a medicament for the treatment of cancer.

According to a further aspect of the present invention there is provided the use of a therapeutic amount of a compound of formula II in the manufacture of a medicament for the treatment of cancer.

According to a further aspect of the present invention there is provided the use of a therapeutic amount of a compound of formula III in the manufacture of a medicament for the treatment of cancer.

Cancer cells suitable for treatment with the compounds described herein may be partially or totally deficient in HR. Preferably, the cells are totally deficient in HR.

The compounds described herein may be used to treat an inherited form of cancer wherein the patient to be treated has a familial predisposition to the cancer. However the said compounds are particularly suitable for the treatment of gene-linked hereditary cancer, and most particularly gene-linked hereditary breast cancer.

In a preferred aspect, the PARP inhibitor is useful in the treatment of cancer cells defective in the expression of a gene involved in HR. Genes with suggested function in HR include XRCC1, ADPRT (PARP-1), ADPRTL2, (PARP02) CTPS, RPA, RPA1, RPA2, RPA3, XPD, ERCC1, XPF, MMS19, RAD51, RAD51β, RAD51C, RAD51D, DMC1, XRCCR, XRCC3, BRCA1, BRCA2, RAD52, RAD54, RAD50, MRE11, NB51, WRN, BLM KU70, KU80, ATM, ATR CHK1, CHK2, FANCA, FANCB, FANCC, FANCD1, FANCD2, FANCE, FANCF, FANCG, FANCC, FANCD1, FANCD2, FANCE, FANCF, FANCG, RAD1, RAD9 [See (2, 3, 5, 22-28) for reviews].

A gene involved in HR may be a tumour suppressor gene. The invention thus provides for the treatment of cancer cells defective in the expression of a tumour suppressor gene. Preferably, the tumour suppressor gene is BRCA1 or BRCA2.

Breast cancer is the most common type of cancer among women in the Western World. Certain families have a strong predisposition for breast cancer, which is often owing to an inherited mutation in one allele of either BRCA1 or BRCA2. However, one functional allele is maintained. Thus, individuals possessing the said mutation develop normally and have no phenotypic consequence from this mutation. However, in one cell, the functional allele might be lost, making this cell cancerous and at the same time deficient in HR. This step is critical for the onset of a tumour (1).

Therefore, according to a still further aspect of the invention there is provided the use of a therapeutic amount of a compound of formula I in the manufacture of a medicament for the treatment of cancer cells defective in BRCA1 and/or BRCA2 expression.

According to a further aspect of the present invention there is provided the use of a therapeutic amount of a compound of formula II in the manufacture of a medicament for the treatment of cancer cells defective in BRCA1 and/or BRCA2 expression.

According to a further aspect of the present invention there is provided the use of a therapeutic amount of a compound of formula III in the manufacture of a medicament for the treatment of cancer cells defective in BRCA1 and/or BRCA2 expression.

The cancer cells to be treated may be partially or totally deficient in BRCA1 or BRCA2 expression. Such deficiencies can be identified using multiplex PCR techniques array techniques (29, 30) or using other screens known to the skilled person. Particularly useful techniques include real-time quantitative RT-PCR, Northern blot, immunohistochemistry and Western Blot (31, 32).

Accordingly, the compounds of the present invention are of particular interest for the treatment of a range of selected cancer tumours, and the invention further provides a method for the treatment of a patient suffering from cancer.

The compounds described herein may be administered in a therapeutically effective non-toxic amount via any suitable route for effectively targeting cancer cells. Suitable administration routes include, but are not limited to, any of the following: oral, intravenous, intramuscular, intradermal, intranasal, or topical.

A therapeutically effective amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease.

For administration to mammals, and particularly humans, it is expected that the daily dosage level of the active agent will be from 0.01 to 50 mg/kg in mice and 0.01 mg/m$^2$ to 50 mg/m$^2$ body surface area in humans. Ultimately, however, the amount of active ingredient administered and the frequency of administration will be at the discretion of a physician.

Advantageously, only very low doses of PARP inhibiting compounds are needed to have a therapeutic effect in treating cancer thereby reducing systemic build up of the compounds and thus minimising any associated toxic effects.

While it may be possible for the compounds described herein to be administered alone as the 'raw' compound, it is preferable to present the compounds in a pharmaceutical composition.

All methods of formulation in making up such pharmaceutical compositions will generally include the step of bringing one of the compounds described herein into association with a carrier which constitutes one or more accessory ingredients. Usually, the formulations are prepared by uniformly and intimately bringing the compound of formula I into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of one of the compounds describe herein; as a powder or granules; or a suspension in an aqueous liquid or non-aqueous liquid such as a syrup, an elixir, an emulsion or a draught. Any one of the compounds described herein may also be presented as a bolus, electuary or paste.

A tablet may be made by compression or moulding, optionally with one or more accessory ingredients. Compressed tables may be prepared by compressing, in a suitable machine, any one of the compounds described herein in a free-flowing form such as a powder or granules, optionally mixed with a binder, lubricant, inert diluent, surface active or dispersing agent. Moulded tables may be made by moulding, in a suitable machine, a mixture of any one of the powdered compound described herein with any suitable carrier.

A syrup may be made by adding any one of the compounds described herein to a concentrated, aqueous solution of a sugar, for example sucrose, to which may be added any desired accessory ingredient. Such accessory ingredient(s) may include flavourings, an agent to retard crystallisation of the sugar or an agent to increase the solubility of any other ingredient, such as a polyhydric alcohol, for example glycerol or sorbitol.

Formulations for rectal administration may be presented as a suppository with a usual carrier such as cocoa butter.

Formulations suitable for parenteral administration conveniently comprise a sterile aqueous preparation of any one of the compounds describe herein which is preferably isotonic with the blood for the recipient.

In addition to the aforementioned ingredients, formulations of this invention, for example ointments, creams and the like, may include one or more accessory ingredients, for example a diluent, buffer, flavouring agent, binder, surface active agent, thickener, lubricant and/or a preservative (including an antioxidant) or other pharmaceutically inert excipient.

The compounds of this invention may also be made up for administration in liposomal formulations which can be prepared by methods well-known in the art.

Thus, according to a further aspect of the present invention there is provided a pharmaceutical composition comprising a compound of formula I, or pharmaceutically acceptable salt thereof, as an active agent.

According to a further aspect of the present invention there is provided a pharmaceutical composition comprising a compound of formula II, or pharmaceutically acceptable salt thereof, as an active agent.

According to a further aspect of the present invention there is provided a pharmaceutical composition comprising a compound of formula III, or pharmaceutically acceptable salt thereof, as an active agent.

The pharmaceutical composition may further comprise at least one other ingredient providing a compatible pharmaceutically acceptable additive, carrier diluent carrier or excipient and may be presented in unit dosage form.

The carrier(s) must be pharmaceutically acceptable in the sense of being compatible with the other ingredients of the formulation and not deterious to the recipient thereof.

The possible formulations include those suitable for oral, rectal, topical and parenteral (including subcutaneous, intramuscular and intravenous) administration or for administration to the lung or another absorptive site such as the nasal passages.

The compounds referred to herein may be administered in combination with other anti-cancer compounds.

The present invention also includes a method of treating cancer in mammals by administering the compounds described herein and their pharmaceutically acceptable salts.

Thus, according to a further aspect of the present invention there is provided a method for the treatment of cancer in mammals comprising administering a compound of formula I, or a pharmaceutically acceptable salt thereof.

Thus, according to a further aspect of the present invention there is provided a method for the treatment of cancer in mammals comprising administering a compound of formula II, or a pharmaceutically acceptable salt thereof:

Thus, according to a further aspect of the present invention there is provided a method for the treatment of cancer in mammals comprising administering a compound of formula III, or a pharmaceutically acceptable salt thereof:

The present invention will now be described by way of example only with reference to the accompanying figures wherein:

FIG. 1 shows the percentage survival of AA8, IrS ISF and CxR3 cell lines when treated with various concentrations of the compound of formula III. Formula III was found to be most active against IrS ISF, which lacks XRCC3, having an $LC_{50}$ (the concentration of the active component that kills 50% of the cells) of 100 nM.

FIG. 2 shows the percentage survival of V79-Z, VC8 and VC8B2 cell lines when treated with various concentrations of the compound of formula III. Formula III was found to be most effective against the VC8 cell line, which lacks BRCA2, having an $LC_{50}$ value of 43 nM and an $LC_{90}$ (concentration of active component that kills 90% of the cells) was 1200 nM.

Figure 3:
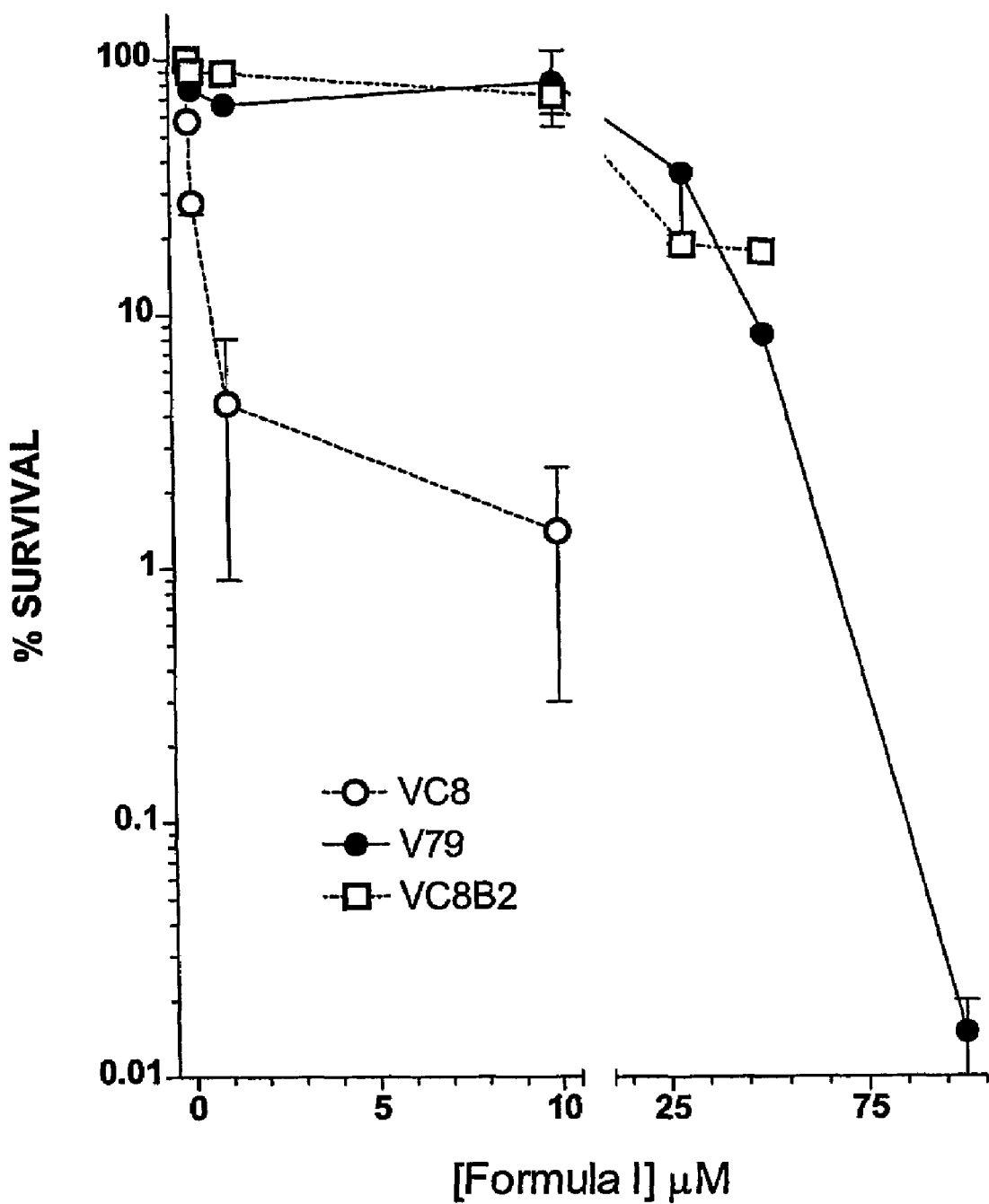
FIG. 3 is a graph showing cell survival in the presence of PARP inhibitor of formula I in V79 cell line, VC8 cell line and VC8B2 cell line.
Figure 4:
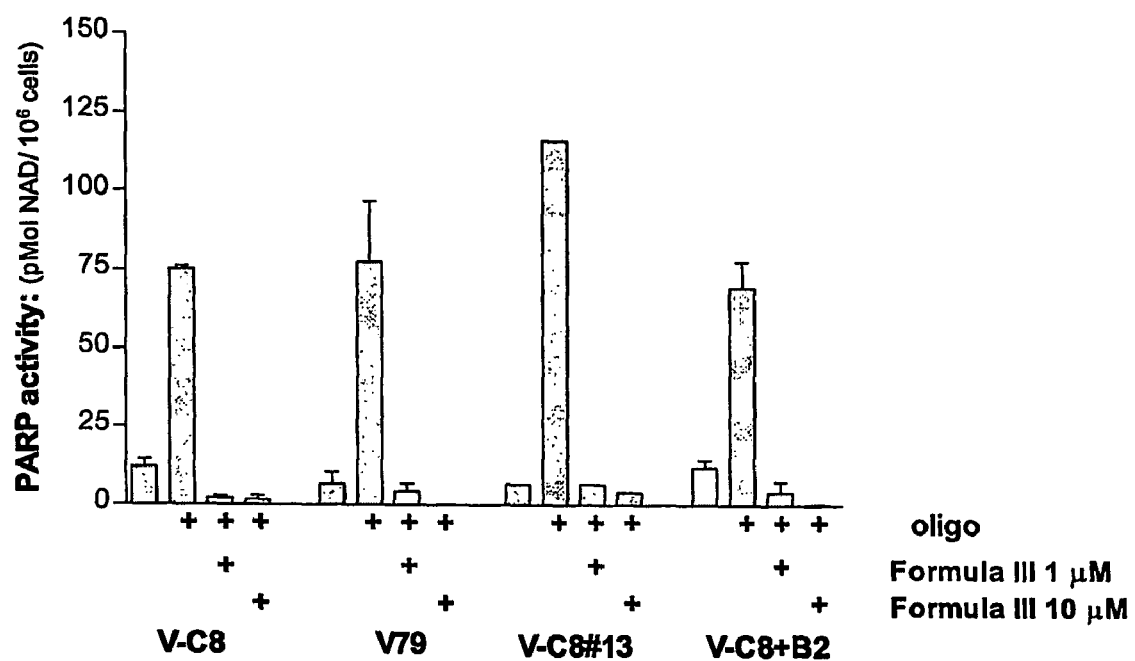
FIG. 4 is a bar chart showing PARP activity in VC8, V79, VC8#13 and VC8, VC8#13 and VC8+B2 cell lines in the presence of PARP inhibitor of formula III.

FIG. 3 shows the percentage survival of V79-Z, VC8 and VC8B2 cell lines when treated with various concentrations of the compound of formula I. Formula I was found to be most effective against the VC8 cell line, which lacks BRCA2, having an $LC_{50}$ value of 12 nM, $LC_{90}$ was 27 nM FIG. 4 shows PARP activity of various cell lines when treated with various concentrations of the compound of formula III. The graph of FIG. 3 is divided into four result sets for each respective cell line. The first bar of each set shows the background PARP activity (no oligo present, so PARP activity is dependent upon endogenous DNA breaks), the second bar is total stimulatable (by oligo) PARP activity and the third and fourth bars show the PARP activity in the presence of the compound of formula III.

Figure 5:
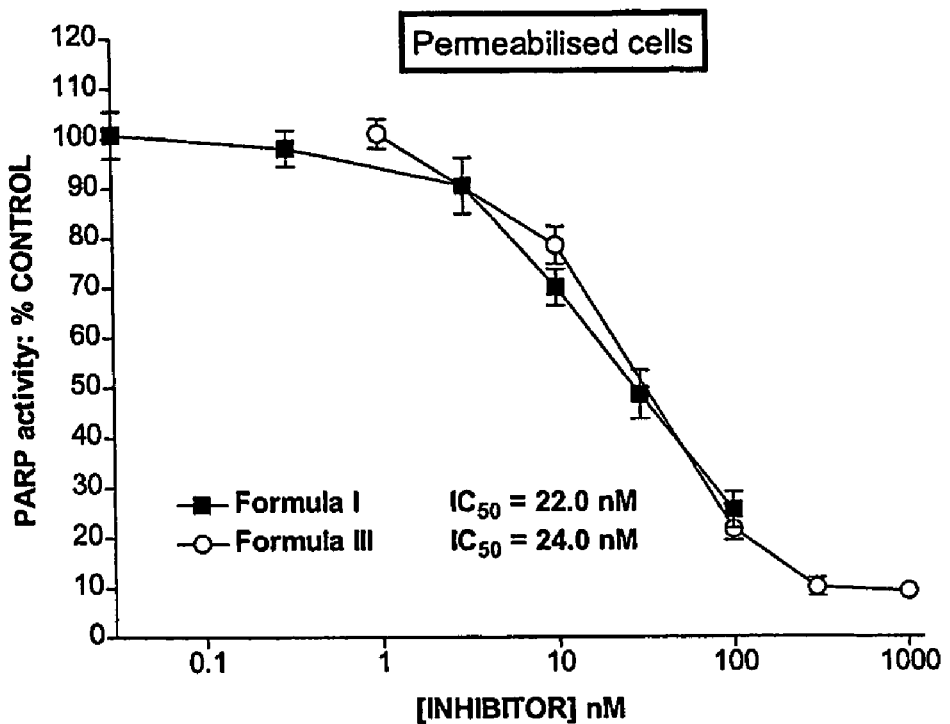
FIG. 5 is a pair of graphs showing inhibition of cellular PARP activity in the presence of PARP inhibitor of formula I and III in permeabilised (upper graph) and intact (lower graph) L1210 cells.
Figure 5:
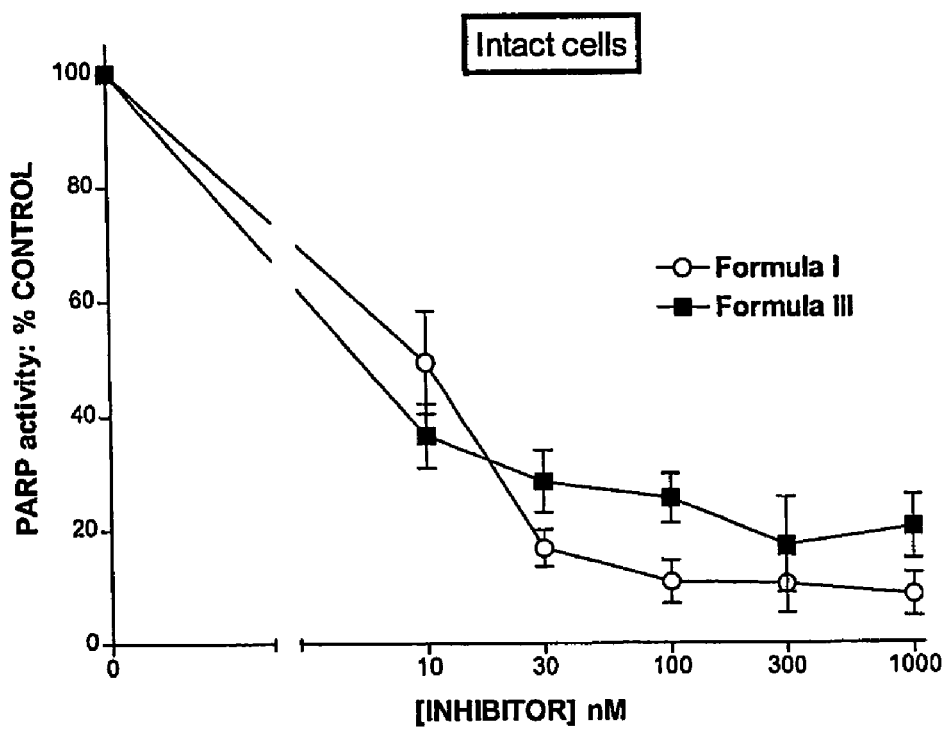

FIG. 5 shows the effect of Compounds Formula I and III on PARP activity.

Cells used to obtain the results shown in FIG. 5 were either permeabilised with digitonin and then assayed for total stimulatable (by oligo) PARP activity in the presence and absence of PARP inhibitor of formula I and formula III or exposed to one of said PARP inhibitors for 20 minutes prior to permeabilisation and assayed for total stimulatable PARP activity.

There was no difference in the PARP inhibitory activity of the compounds of formula I and formula III when the cells were permeabilised prior to adding the inhibitor compound but the compound of formula I was more potent in intact cells, possibly because it accumulates within cells to a higher degree.

Figure 6:
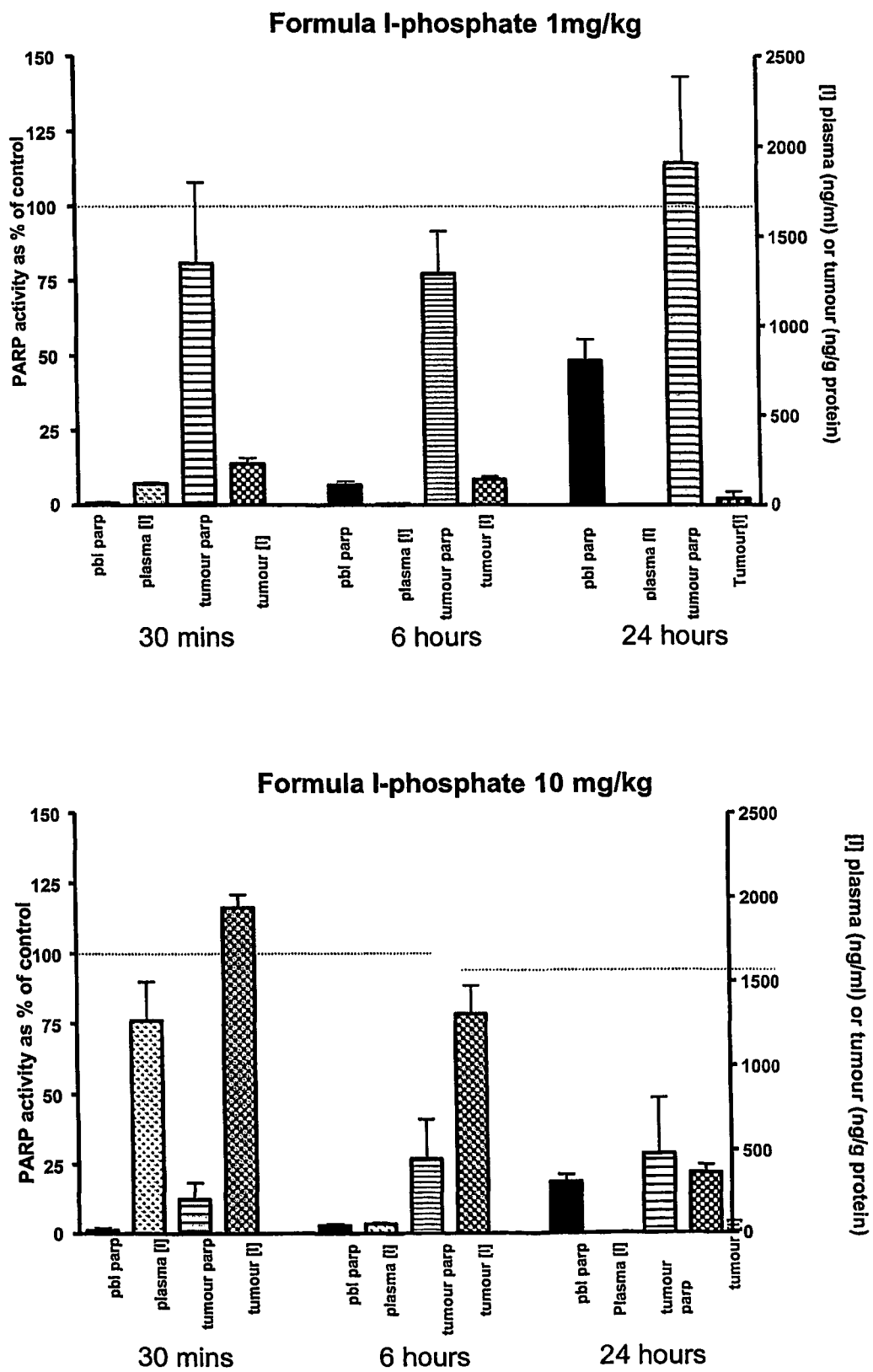
FIG. 6 is a pair of bar charts showing the blood and tumour pharmacokinetics and pharmacodynamics with formula I-phosphate at 1 mg/kg (upper) and 10 mg/kg (lower) in mice bearing SW620 xenografts.

FIG. 6 shows the plasma and tumour concentrations of the compound of formula I, and its pharmacokinetic effect on mouse peripheral blood lymphocytes (pbl parp) and SW620 xenografts (tumour PARP), at various times following intraperitoneal administration of the phosphate salt of compound of formula I. The phosphate salt of the compound of formula I increases the solubility of formula I. However, on administration to an animal (including human) plasma phosphatases break the phosphate salt of formula I (formula I-phosphate) down to the parent compound i.e. formula I.

It is evident form FIG. 6 that thirty minutes after administration of formula I-phosphate at 10 mg/kg high levels of the parent compound were detected in both plasma and tumour. The concentration of formula 1 decreased with time more rapidly in the plasma than in the tumour and at 24 hr after administration significant levels were detectable in the tumour but none could be detected in the plasma. There was a profound and sustained inhibition of PARP activity in both pbls and tumour: <50% control up to 24 hr.

After administration of formula I-phosphate at 1 mg/kg lower levels of the compound of formula I can be found in both the plasma and tumour and consequently there was a less pronounced effect on PARP activity.

Figure 7:
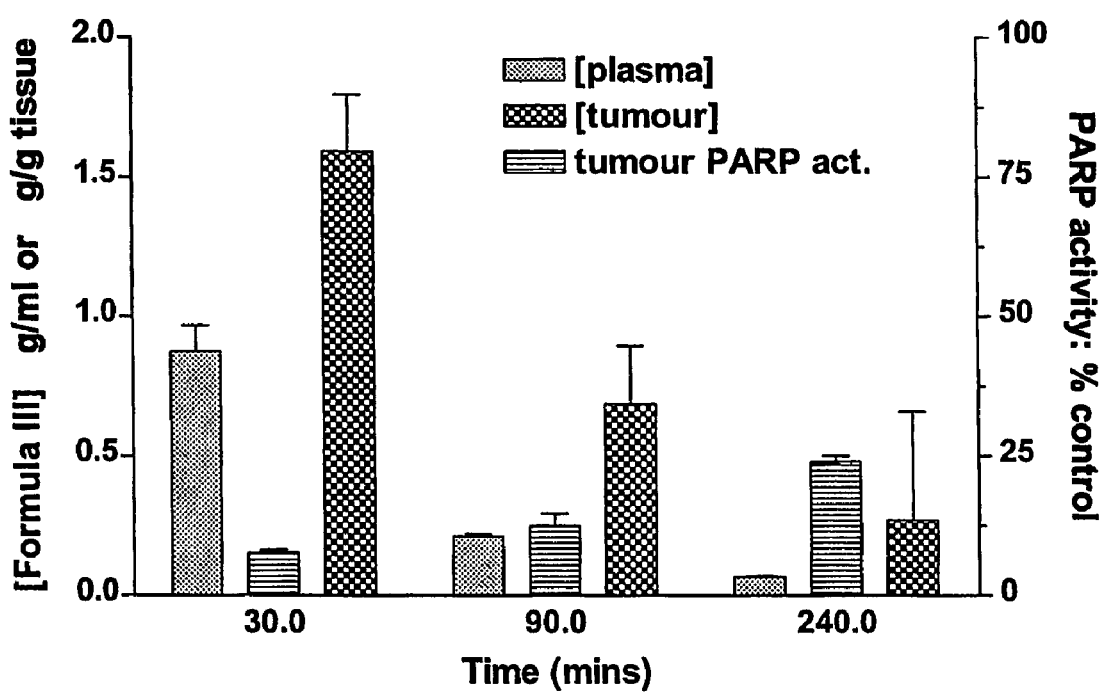
FIG. 7 is a bar chart showing the pharmacokinetics and pharmacodynamics with formula III in mice bearing SW620 xenografts.

FIG. 7 shows the plasma and tumour concentrations of the compound of formula III, and its pharmacokinetic effect on SW620 xenografts (tumour PARP act), at various times following intraperitoneal administration of the 10 mg/kg of compound of formula III. This compound also distributes well to the tumour and is preferentially retained with time and similarly inhibits PARP activity in the tumour.

Figure 8:
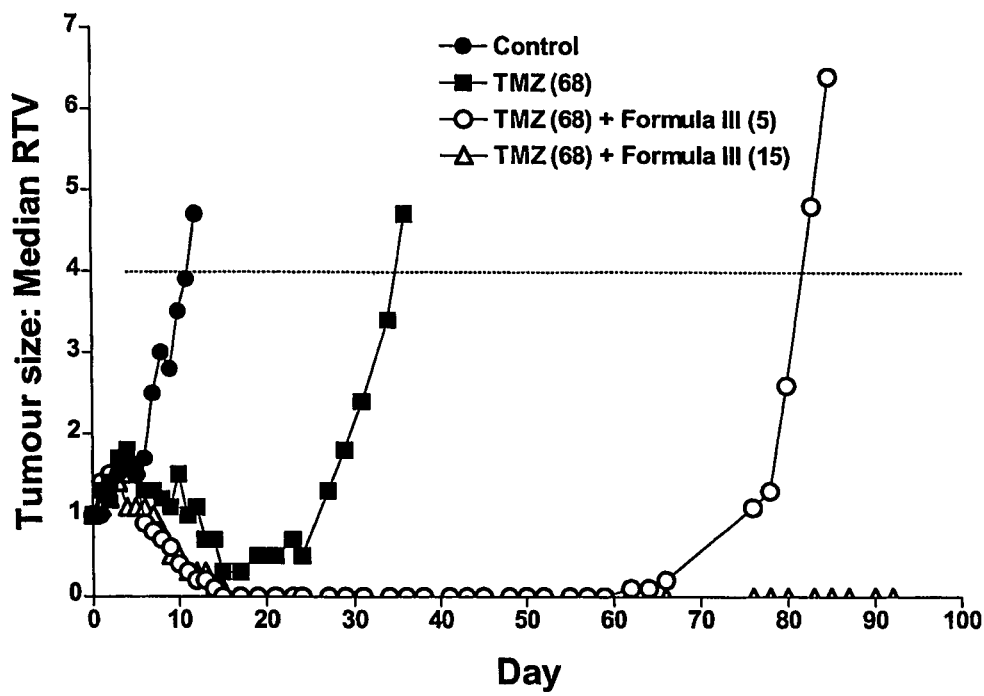
FIG. 8 is a graph showing the tumour growth (median relative tumour volume) in mice bearing SW620 xenografts following treatment with formula III in combination with temozolomide (TMZ) and with TMZ alone.

FIG. 8 shows that for 20 days from administration of ternolozomide (68 mg/kg daily×5) the tumour xenograft has progressively reduced in size. However, shortly after this time the tumour size begins to increase. When a compound of formula III (5 mg/kg daily×5) is administered in conjunction with temozolomide the tumour shrinks significantly for around 15 days, to an undetectable size, the tumour size remains undetectable for a further 50 days thereafter when it begins to increase in size. When a larger dose of formula III (15 mg/kg daily×5) is administered the tumour size remains undetectable for a further 80 days until the end of the experiment when no tumour was detectable at autopsy i.e. complete tumour regression.

Figure 9:
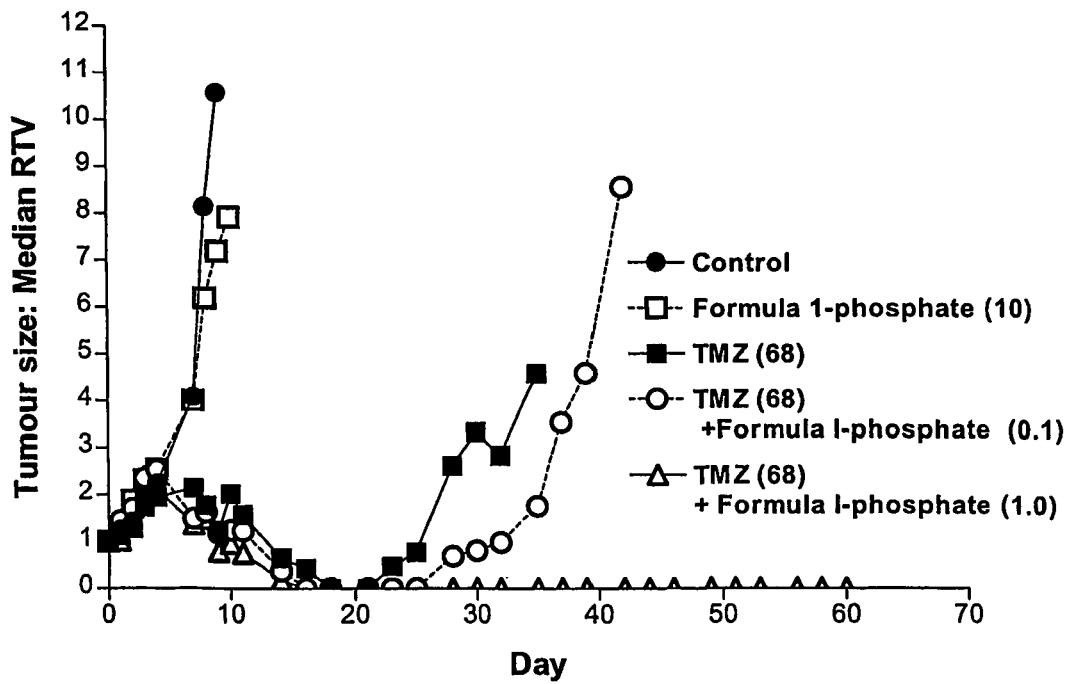
FIG. 9 is a graph showing the tumour growth (median relative tumour volume) of mice bearing SW620 xenografts following treatment with formula I-phosphate in combination with temozolomide (TMZ) and with formula I-phosphate and TMZ alone.

FIG. 9 shows a similar pattern to that seen in FIG. 8 following the administration of formula I-phosphate (at 0.1 mg/kg and 1.0 mg/kg) in combination with temolozomide.

Toxicity Assay—Clonogenic Survival Assay

Figure 1:
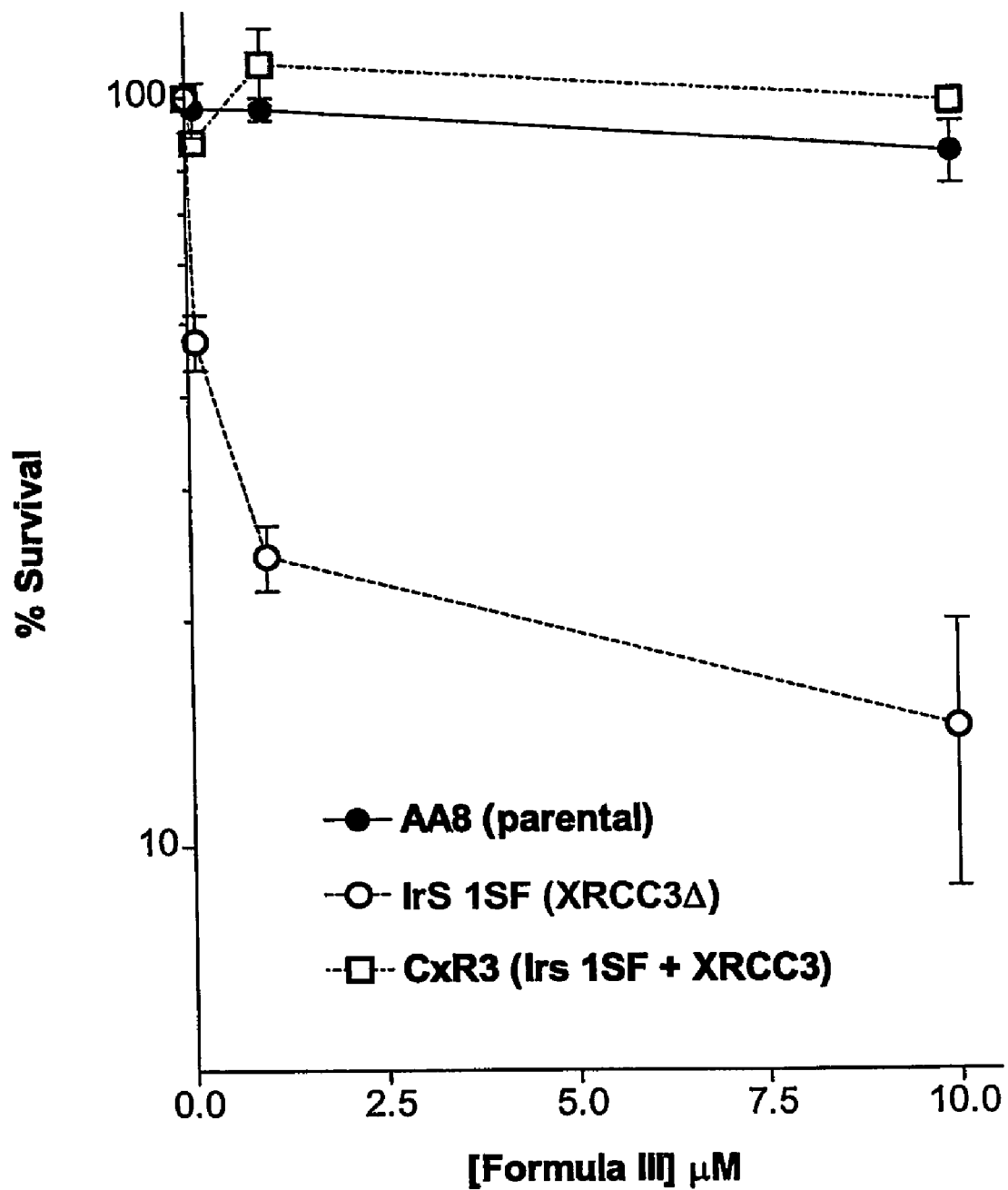
FIG. 1 is a graph showing cell survival in the presence of PARP inhibitor of formula III in AA8 cell line, IsrISF cell line and CxR3 cell line.
Figure 2:
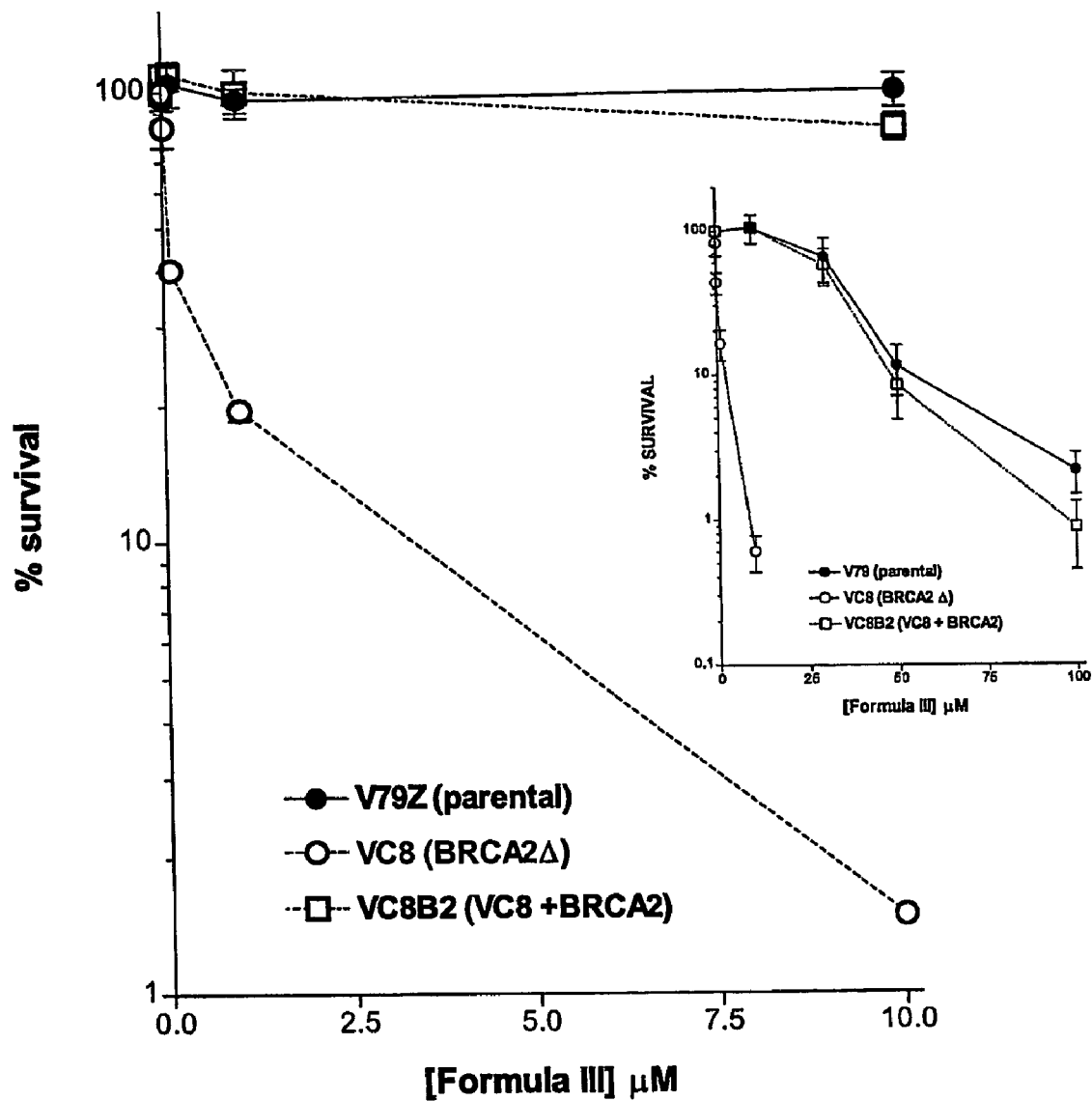
FIG. 2 is a graph showing cell survival in the presence of PARP inhibitor of formula III in V79 cell line, VC8 cell line and VC8B2 cell line.

Exponentially growing cells in 6-well plates were exposed to the compound of formula III at the concentrations indicated in FIG. 2 in 1% DMSO or 1% DMSO alone in medium for 24 hours.

The cells were harvested by trypsinisation, counted and seeded at varying densities in 10 cm dishes in fresh medium in the absence of drug for colony formation.

7-10 days later the dishes were fixed with methanol:acetic acid 3:1 and stained with 0.4% crystal violet.

Colonies were counted and the survival relative to 1% DMSO control treated cells calculated.

PARP Activity Assay

Exponentially growing cells were exposed to 1% DMSO in culture medium (control) or a compound of formula I or III in 1% DMSO at the concentrations indicated in FIG. 4 to cells permeabilised with digitonin, or intact cells for 20 minutes prior to washing and digitonin-permeabilization. PARP activity was measured by incorporation of a [32P] labelled NAD+ substrate into TCA precipitateble polymers after stimulation by the addition of a blunt-ended oligonucleotide and compared with non-oligonucleotide-stimulated cells. PARP activity in tumour homogenates (1 in 40 in isotonic buffer) from formula III-treated mice was measured in the same way.

TABLE 1

Genotype and origin of cell lines used in this study.

| Cell line | Genotype | Defect | Origin | Reference | Comments |
|---|---|---|---|---|---|
| AA8 | wt | wt | CHO | [41] | Chinese hamster ovary cell line |
| irs1SF | XRCC3− | XRCC3−, deficient in HR | AA8 | [41] | Radiation-sensitive cell line derived from AA8 which lacks XRCC3 a component of HR pathway |
| CXR3 | XRCC3− + hXRCC3 | wt | irs1SF | [41] | irs1SF transfected with hXRCC3 gene |
| V79-Z | wt | wt | V79 | [42] | V79 are hamster lung fibroblasts |
| VC8 | BRCA2− | BRCA2−, deficient in HR | V79-Z | [42] | VC8 are radiation sensitive derivatives of V79 which are deficient in BRCA2 |
| VC8#13 | BRCA2− + hBRCA2 | wt | VC8 | [42] | VC8 with chromosome 13 containing hBRCA2 |
| VC8 + B2 | BRCA2− + hBRCA2 | wt | VC8 | [42] | VC8 transfected with HBRCA2 |

Materials and Methods

Cytotoxicity of PARP Inhibitors to Cells Deficient in HR (XRCC3 or BRCA2)

Cell Culture

The AA8, irs1SF and CXR3 cell lines were provided by Larry Thompson [41].

The VC-8, VC-8+B2, VC-8#13 were a gift from Malgorzata Zdienicka [42]. All cell lines in this study were grown in Dulbecco's modified Eagle's Medium (DMEM) with 10% Foetalbovine serum and penicillin (100 U/ml) and streptomycin sulphate (100 μg/mL) at 37° C. under an atmosphere containing 5% $CO_2$.

PARP activity in pbls and tumour homogenates from formula I-phosphate treated mice was measured by immunological detection of polymer using the 10H antibody. Briefly, tumour homogenates diluted to up to 1:1000 in isotonic buffer were incubated with 350 μM NAD for 6 min and blotted onto nitrocellulose membrane. The poly(ADP-ribose) (PAR) polymer formation was quantified by chemiluminescence detection using a Fuji LAS3000 UV Illuminator by reference to serial dilutions of a PAR standard, following incubation with 10H antibody to PAR and a secondary anti-mouse antibody. The results were standardised by reference to the measured protein content of the homogenate.

It is of course to be understood that the invention is not intended to be restricted to the details of the above embodiments which are described by way of example only.

REFERENCES

[1] C. Lundin, K. Erixon, C. Arnaudeau, N. Schultz, D. Jenssen, M. Meuth and T. Helleday Different roles for nonhomologous end joining and homologous recombination following replication arrest in mammalian cells, Mol Cell Biol 22 (2002) 5869-5878.

[2] A. R. Venkitaraman Cancer susceptibility and the functions of BRCA1 and BRCA2, Cell 108 (2002) 171-182.

[3] D. D'Amours, S. Desnoyers, I. D'Silva and G. G. Poirier Poly(ADP-ribosyl)ation reactions in the regulation of nuclear functions, Biochem J 342 (1999) 249-268.

[4] Z. Herceg and Z. Q. Wang Functions of poly(ADP-ribose) polymerase (PARP) in DNA repair, genomic integrity and cell death, Mutat Res 477 (2001) 97-110.

[5] T. Lindahl, M. S. Satoh, G. G. Poirier and A. Klungland Post-translational modification of poly(ADP-ribose) polymerase induced by DNA strand breaks, Trends Biochem Sci 20 (1995) 405-411.

[6] M. S. Satoh and T. Lindahl Role of poly(ADP-ribose) formation in DNA repair, Nature 356 (1992) 356-358.

[7] S. Shall and G. de Murcia Poly(ADP-ribose) polymerase-1: what have we learned from the deficient mouse model?, Mutat Res 460 (2000) 1-15.

[8] Z. Q. Wang, L. Stingl, C. Morrison, M. Jantsch, M. Los, K. Schulze-Osthoff and E. F. Wagner PARP is important for genomic stability but dispensable in apoptosis, Genes Dev 11 (1997) 2347-2358.

[9] C. M. Simbulan-Rosenthal, B. R. Haddad, D. S. Rosenthal, Z. Weaver, A. Coleman, R. Luo, H. M. Young, Z. Q. Wang, T. Ried and M. E. Smulson Chromosomal aberrations in PARP(−/−) mice: genome stabilization in immortalized cells by reintroduction of poly(ADP-ribose) polymerase cDNA, Proc Natl Acad Sci USA 96 (1999) 13191-13196.

[10] J. M. de Murcia, C. Niedergang, C. Trucco, M. Ricoul, B. Dutrillaux, M. Mark, F. J. Oliver, M. Masson, A. Dierich, M. LeMeur, C. Walztinger, P. Chambon and G. de Murcia Requirement of poly(ADP-ribose) polymerase in recovery from DNA damage in mice and in cells, Proc Natl Acad Sci USA 94 (1997) 7303-7307.

[11] F. d'Adda di Fagagna, M. P. Hande, W. M. Tong, P. M. Lansdorp, Z. Q. Wang and S. P. Jackson Functions of poly(ADP-ribose) polymerase in controlling telomere length and chromosomal stability, Nat Genet 23 (1999) 76-80.

[12] E. Samper, F. A. Goytisolo, J. Menissier-de Murcia, E. Gonzalez-Suarez, J. C. Cigudosa, G. de Murcia and M. A. Blasco Normal telomere length and chromosomal end capping in poly(ADP-ribose) polymerase-deficient mice and primary cells despite increased chromosomal instability, J Cell Biol 154 (2001) 49-60.

[13] C. Morrison, G. C. Smith, L. Stingl, S. P. Jackson, E. F. Wagner and Z. Q. Wang Genetic interaction between PARP and DNA-PK in V(D)J recombination and tumorigenesis, Nat Genet 17 (1997) 479-482.

[14] V. Schreiber, D. Hunting, C. Trucco, B. Gowans, D. Grunwald, G. De Murcia and J. M. De Murcia A dominant-negative mutant of human poly(ADP-ribose) polymerase affects cell recovery, apoptosis, and sister chromatid exchange following DNA damage, Proc Natl Acad Sci USA 92 (1995) 4753-4757.

[15] J. H. Kupper, M. Muller and A. Burkle Trans-dominant inhibition of poly(ADP-ribosyl)ation potentiates carcinogen induced gene amplification in SV40-transformed Chinese hamster cells, Cancer Res 56 (1996) 2715-2717.

[16] J. Magnusson and C. Ramel Inhibitor of poly(ADP-ribose)transferase potentiates the recombinogenic but not the mutagenic action of alkylating agents in somatic cells in vivo in *Drosophila melanogaster*, Mutagenesis 5 (1990) 511-514.

[17] A. S. Waldman and B. C. Waldman Stimulation of intrachromosomal homologous recombination in mammalian cells by an inhibitor of poly(ADP-ribosylation), Nucleic Acids Res 19 (1991) 5943-5947.

[18] A. Semionov, D. Cournoyer and T. Y. Chow Inhibition of poly(ADP-ribose)polymerase stimulates extrachromosomal homologous recombination in mouse Ltk-fibroblasts, Nucleic Acids Res 27 (1999) 4526-4531.

[19] F. Dantzer, V. Schreiber, C. Niedergang, C. Trucco, E. Flatter, G. De La Rubia, J. Oliver, V. Rolli, J. Menissier-de Murcia and G. de Murcia Involvement of poly(ADP-ribose) polymerase in base excision repair, Biochimie 81 (1999) 69-75.

[20] F. Dantzer, G. de La Rubia, J. Menissier-De Murcia, Z. Hostomsky, G. de Murcia and V. Schreiber Base excision repair is impaired in mammalian cells lacking Poly(ADP-ribose) polymerase-1, Biochemistry 39 (2000) 7559-7569.

[21] L. Tentori, I. Portarena and G. Graziani Potential clinical applications of poly(ADP-ribose) polymerase (PARP) inhibitors, Pharmacol Res 45 (2002) 73-85.

[22] T. Lindahl and R. D. Wood Quality control by DNA repair, Science 286 (1999) 1897-1905.

[23] K. W. Caldecott DNA single-strand break repair and spinocerebellar ataxia, Cell 112 (2003) 7-10.

[24] D. D'Amours and S. P. Jackson The Mre11 complex: at the crossroads of dna repair and checkpoint signaling, Nat Rev Mol Cell Biol 3 (2002) 317-327.

[25] A. D. D'Andrea and M. Grompe The Fanconi anaemia/BRCA pathway, Nat Rev Cancer 3 (2003) 23-34.

[26] S. P. Jackson Sensing and repairing DNA double-strand breaks, Carcinogenesis 23 (2002) 687-696.

[27] R. Kanaar, J. H. Hoeijmakers and D. C. van Gent Molecular mechanisms of DNA double strand break repair, Trends Cell Biol 8 (1998) 483-489.

[28] D. C. van Gent, J. H. Hoeijmakers and R. Kanaar Chromosomal stability and the DNA double-stranded break connection, Nat Rev Genet 2 (2001) 196-206.

[29] S. L. Neuhausen and E. A. Ostrander Mutation testing of early-onset breast cancer genes BRCA1 and BRCA2, Genet Test 1 (1997) 75-83.

[30] G. Kuperstein, W. D. Foulkes, P. Ghadirian, J. Hakimi and S. A. Narod A rapid fluorescent multiplexed-PCR analysis (FMPA) for founder mutations in the BRCA1 and BRCA2 genes, Clin Genet 57 (2000) 213-220.

[31] Vissac-Sabatier C, Coxam V, Dechelotte P, Picherit C, Horcajada M-N, Davicco M-J, Lebecque P, Bignon Y-J, and Bernard-Gallon D. Phytoestrogen-rich diets modulate expression of BRCA1 and BRCA2 tumour suppressor genes in mammary glands of female Wistar rats. Cancer Research vol 63 pp 6607-6612 (2003).

[32] Wu K, Jiang S-W and Couch F J. p53 mediates repression of the BRCA2 promoter and down regulation of BRCA2 mRNA and protein levels in response to DNA damage. J. Biol. Chem. Vol 278 pp 15652-15660 (2003).

[33] A. Chiarugi Poly(ADP-ribose) polymerase: killer or conspirator? The 'suicide hypothesis' revisited, Trends Pharmacol Sci 23 (2002) 122-129.

[34] C. R. Calabrese, M. A. Batey, H. D. Thomas, B. W. Durkacz, L. Z. Wang, S. Kyle, D. Skalitzky, J. Li, C. Zhang, T. Boritzki, K. Maegley, A. H. Calvert, Z. Hostomsky, D. R. Newell and N. J. Curtin Identification of Potent Nontoxic Poly(ADP-Ribose) Polymerase-1 Inhibitors: Chemopotentiation and Pharmacological Studies, Clin Cancer Res 9 (2003) 2711-2718.

[35] D. Ferraris, Y. S. Ko, T. Pahutski, R. P. Ficco, L. Serdyuk, C. Alemu, C. Bradford, T. Chiou, R. Hoover, S. Huang, S. Lautar, S. Liang, Q. Lin, M. X. Lu, M. Mooney, L. Morgan, Y. Qian, S. Tran, L. R. Williams, Q. Y. Wu, J. Zhang, Y. Zou and V. Kalish Design and synthesis of poly ADP-ribose polymerase-1 inhibitors. 2. Biological evaluation of aza-5 [H]-phenanthridin-6-ones as potent, aqueous-soluble compounds for the treatment of ischemic injuries, J Med Chem 46 (2003) 3138-3151.

[36] K. J. Dillon, G. C. Smith and N. M. Martin A FlashPlate assay for the identification of PARP-1 inhibitors, J Biomol Screen 8 (2003) 347-352.

[37] A. J. Pierce, R. D. Johnson, L. H. Thompson and M. Jasin XRCC3 promotes homology-directed repair of DNA damage in mammalian cells, Genes Dev 13 (1999) 2633-2638.

[38] R. D. Johnson, N. Liu and M. Jasin Mammalian XRCC2 promotes the repair of DNA double-strand breaks by homologous recombination, Nature 401 (1999) 397-399.

[39] G. M. Shah, D. Poirier, S. Desnoyers, S. Saint-Martin, J. C. Hoflack, P. Rong, M. ApSimon, J. B. Kirkland and G. G. Poirier Complete inhibition of poly(ADP-ribose) polymerase activity prevents the recovery of C3H10T1/2 cells from oxidative stress, Biochim Biophys Acta 1312 (1996) 1-7.

[40] R. J. Griffin, S. Srinivasan, K. Bowman, A. H. Calvert, N. J. Curtin, D. R. Newell, L. C. Pemberton and B. T. Golding Resistance-modifying agents. 5. Synthesis and biological properties of quinazolinone inhibitors of the DNA repair enzyme poly(ADP-ribose) polymerase (PARP), J Med Chem 41 (1998) 5247-5256.

[41] S. Boulton, L. C. Pemberton, J. K. Porteous, N. J. Curtin, R. J. Griffin, B. T. Golding and B. W. Durkacz Potentiation of temozolomide-induced cytotoxicity: a comparative study of the biological effects of poly(ADP-ribose) polymerase inhibitors, Br J Cancer 72 (1995) 849-856.

[42] C. S. Griffin, P. J. Simpson, C. R. Wilson and J. Thacker Mammalian recombination-repair genes XRCC2 and XRCC3 promote correct chromosome segregation, Nat Cell Biol 2 (2000) 757-761.

[43] R. S. Tebbs, Y. Zhao, J. D. Tucker, J. B. Scheerer, M. J. Siciliano, M. Hwang, N. Liu, R. J. Legerski and L. H. Thompson Correction of chromosomal instability and sensitivity to diverse mutagens by a cloned cDNA of the XRCC3 DNA repair gene, Proc Natl Acad Sci USA 92 (1995) 6354-6358.

[44] M. Kraakman-van der Zwet, W. J. Overkamp, R. E. van Lange, J. Essers, A. van Duijn-Goedhart, I. Wiggers, S. Swaminathan, P. P. van Buul, A. Errami, R. T. Tan, N. G. Jaspers, S. K. Sharan, R. Kanaar and M. Z. Zdzienicka Brca2 (XRCC11) deficiency results in radioresistant DNA synthesis and a higher frequency of spontaneous deletions, Mol Cell Biol 22 (2002) 669-679.

The invention claimed is:

1. A method for treating cancer in a mammal, wherein the cancer is of a type that is caused by a genetic defect in a gene that mediates homologous recombination and is selected from the group consisting of cancer of the: breast, lung, colon, pancreas, stomach, ovary, cervix, breast, prostate, bone, brain, and skin, the gene that mediates homologous recombination being selected from the group consisting of: XRCC1, CTPS, RPA, RPA1, RPA2, RPA3, XPD, ERCC1, XPF, MMS19, RAD51, RAD51, RAD51C, RAD51D, DMC1, XRCCR, XRCC3, BRCA1, BRCA2, RAD52, RAD54, RAD50, MRE11, NB51, WRN, BLM KU70, KU80, ATM, ATR CHK1, CHK2, FANCA, FANCB, FANCC, FANCD1, FANCD2, FANCE, FANCF, FANCG, FANCC, FANCD1, FANCD2, FANCE, FANCF, FANCG, RAD1, RAD9 and combinations thereof, the method comprising:

selecting the mammal having said genetic defect; and administering to the mammal a compound selected from the group consisting of a compound of the formula I, formula II and formula III:

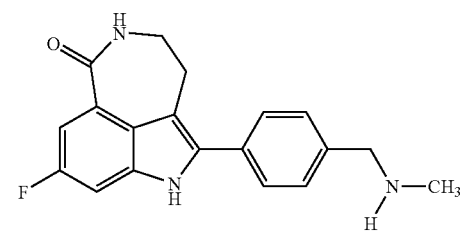

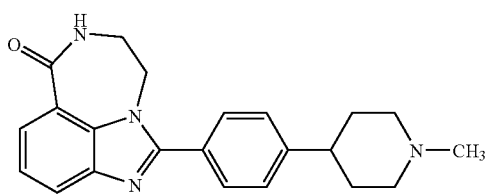

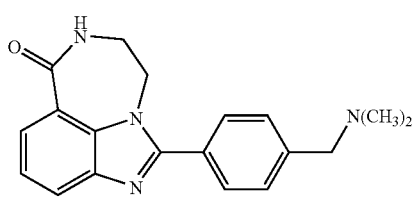

or a pharmaceutically acceptable salt thereof.

2. The method according to claim 1, wherein the compound is the compound of the formula I.

3. The method according to claim 2, wherein the compound of the formula I is in the form of a phosphate salt.

4. The method of claim 1, wherein the cancer is breast cancer.

5. The method of claim 1, wherein the genetic detect is the absence of a gene encoding a protein involved in homologous recombination.

6. The method of claim 1, wherein the genetic defect is in the expression of a gene encoding a protein involved in homologous recombination.

7. The method of claim 1, wherein the gene that mediates homologous recombination is a tumor suppressor gene.

8. The method of claim 7, wherein the tumor suppressor gene is BRCA1 and/or BRCA2.

9. A method for inducing apoptosis of cells defective in a gene that mediates homologous recombination, the cells being cancer cells selected from the group consisting of cancer cells of the: breast, lung, colon, pancreas, stomach, ovary, cervix, breast, prostate, bone, brain, and skin, the gene that mediates homologous recombination being selected from the group consisting of XRCC1, CTPS, RPA, RPA1, RPA2, RPA3, XPD, ERCC1, XPF, MMS19, RAD51, RAD51β, RAD51C, RAD51D, DMC1, XRCCR, XRCC3, BRCA1, BRCA2, RAD52, RAD54, RAD50, MRE11, NB51, WRN, BLM KU70, KU80, ATM, ATR CHK1, CHK2, FANCA, FANCB, FANCC, FANCD1, FANCD2, FANCE, FANCF, FANCG, FANCC, FANCD1, FANCD2, FANCE, FANCF, FANCG, RAD1, RAD9 and combinations thereof, the method comprising:

selecting the cancer cells having said genetic defect; and administering to the cancer cells a compound selected from the group consisting of a compound of the formula I, formula II and formula III:

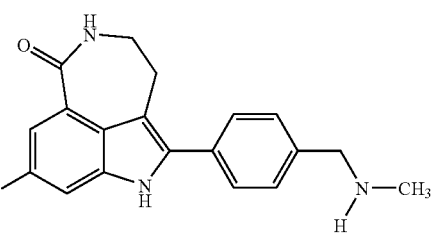

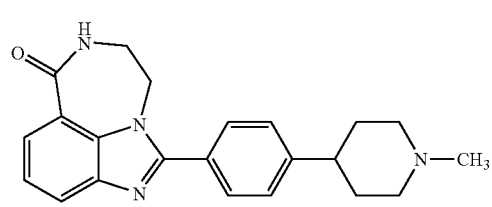

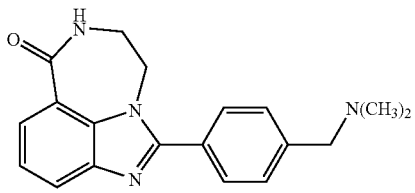 III or a pharmaceutically acceptable salt thereof.

10. The method according to claim 9, wherein the compound is the compound of the formula I.

11. The method according to claim 10, wherein the compound of the formula I is in the form of a phosphate salt.

12. The method of claim 9, wherein the genetic defect of the cells is the absence of a gene encoding a protein involved in homologous recombination.

13. The method of claim 9, wherein the genetic defect of the cells is in the expression of a gene encoding a protein involved in homologous recombination.

14. The method of claim 9, wherein the gene that mediates homologous recombination is a tumor suppressor gene.

15. The method of claim 9, wherein the tumor suppressor gene is BRCA1 and/or BRCA2 and the cancer cells are selected from the group consisting of cancer cells of the: lung, colon, pancreas, stomach, ovary, cervix, breast, prostate, bone, brain, and skin.

* * * * *

SEQUENCE LISTING

<160> NUMBER OF SEQ ID NOS: 6

<210> SEQ ID NO 1
<211> LENGTH: 5468
<212> TYPE: DNA
<213> ORGANISM: Homo sapiens

<400> SEQUENCE: 1

```
cgcccgccca gccccggggg cagggaaagc ctaaattacg gaattaccgc gagcaaggag        60
cgcggaatcg gggagcgtcc ggagctagct ggatcctcta ggcaggatgg tgatgggaat       120
ctttgcaaat tgtatcttct gtttgaaagt gaagtactta cctcagcagc agaagaaaaa       180
gctacaaact gacattaagg aaaatggcgg aaagttttcc ttttcgttaa atcctcagtg       240
cacacatata atcttagata atgctgatgt tctgagtcag taccaactga attctatcca       300
aaagaaccac gttcatattg caaacccaga ttttatatgg aaatctatca gagaaaagag       360
actcttggat gtaaagaatt atgatcctta taagccctg gacatcacac cacctcctga       420
tcagaaggcg agcagttctg aagtgaaaac agaaggtcta tgcccggaca gtgccacaga       480
ggaggaagac actgtggaac tcactgagtt tggtatgcag aatgttgaaa ttcctcatct       540
tcctcaagat tttgaagttg caaaatataa caccttggag aaagtgggaa tggagggagg       600
ccaggaagct gtggtggtgg agcttcagtg ttcgcgggac tccagggact gtcctttcct       660
gatatcctca cacttcctcc tggatgatgg catggagact agaagacagt ttgctataaa       720
gaaaacctct gaagatgcaa gtgaatactt tgaaaattac attgaagaac tgaagaaaca       780
aggatttcta ctaagagaac atttcacacc tgaagcaacc caattagcat ctgaacaatt       840
```

```
gcaagcattg cttttggagg aagtcatgaa ttcaagcact ctgagccaag aggtgagcga    900
tttagtagag atgatttggg cagaggccct gggccacctg aacacatgc ttctcaagcc     960
agtgaacagg attagcctca acgatgtgag caaggcagag gggattctcc ttctagtaaa   1020
ggcagcactg aaaaatggag aaacagcaga gcaattgcaa aagatgatga cagagttta    1080
cagactgata cctcacaaag gcacaatgcc caaagaagtg aacctgggac tattggctaa   1140
gaaagcagac ctctgccagc taataagaga catggttaat gtctgtgaaa ctaatttgtc   1200
caaacccaac ccaccatccc tggccaaata ccgagctttg aggtgcaaaa ttgagcatgt   1260
tgaacagaat actgaagaat tctcagggt tagaaaagag gttttgcaga atcatcacag   1320
taagagccca gtggatgtct tgcagatatt tagagttggc agagtgaatg aaaccacaga   1380
gtttttgagc aaacttggta atgtgaggcc cttgttgcat ggttctcctg tacaaaacat   1440
cgtgggaatc ttgtgtcgag ggttgctttt acccaaagta gtggaagatc gtggtgtgca   1500
aagaacagac gtcggaaacc ttggaagtgg gatttatttc agtgattcgc tcagtacaag   1560
tatcaagtac tcacacccgg gagagacaga tggcaccaga ctcctgctca tttgtgacgt   1620
agccctcgga aagtgtatgg acttacatga gaaggacttt tccttaactg aagcaccacc   1680
aggctacgac agtgtgcatg gagttttcaca acagcctct gtcaccacag actttgagga   1740
tgatgaattt gttgtctata aaccaatca ggttaaaatg aatatatta ttaaattttc   1800
catgcctgga gatcagataa aggactttca tcctagtgat catactgaat tagaggaata   1860
cagacctgag ttttcaaatt tttcaaaggt tgaagattac cagttaccag atgccaaaac   1920
ttccagcagc accaaggccg gcctccagga tgcttctggg aacttggttc ctctggagga   1980
tgtccacatc aaagggagaa tcatagacac tgtagcccag gtcattgttt ttcagacata   2040
cacaaataaa agtcacgtgc ccattgaggc aaaatatatc tttcctttgg atgacaaggc   2100
cgctgtgtgt ggcttcgaag ccttcatcaa tgggaagcac atagtggag agattaaaga   2160
gaaggaagaa gcccagcaag agtacctaga agccgtgacc cagggccatg cgcttacct   2220
gatgagtcag gatgctccgg acgttttac tgtaagtgtt ggaaacttac ccctaaggc   2280
taaggttctt ataaaaatta cctacatcac agaactcagc atcctgggca ctgttggtgt   2340
cttttcatg cccgccaccg tagcacccty gcaacaggac aaggctttga atgaaaacct   2400
tcaggataca gtagagaaga tttgtataaa agaaatagga acaaagcaaa gcttctcttt   2460
gactatgtct attgagatgc cgtacgtgat tgaattcatt ttcagtgata ctcatgaact   2520
gaaacaaaag cgcacagact gcaaagctgt cattagcacc atggaaggca gctccttaga   2580
cagcagtgga ttttctctcc acatcggttt gtctgctgcc tatctcccaa gaatgtgggt   2640
tgaaaaacat ccagaaaaag aaagcgaggc ttgcatgctt gtctttcaac ccgatctcga   2700
tgtcgacctc cctgacctag ccaatgagag cgaagtgatt atttgtcttg actgctccag   2760
ttccatggag ggtgtgacat tcttgcaagc caaggaaatc gccttgcatg cgctgtcctt   2820
ggtgggtgag aagcagaaag taaatattat ccagttcggc acaggttaca aggagctatt   2880
ttcgtatcct aagcatatca caagcaatac cgcggcagca gagttcatca tgtctgccac   2940
acctaccatg gggaacacag acttctggaa aacactccga tatcttagct tattgtaccc   3000
tgctcgaggg tcacggaaca tcctcctggt gtctgatggg caccctccagg atgagagcct   3060
gacattacag ctcgtgaaga ggagccgcc gcacaccagg ttattcgcct gcggtatcgg   3120
ttctacagca aatcgtcacg tcttaaggat tttgtcccag tgtggtgccg gagtatttga   3180
```

-continued

```
atattttaat gcaaaatcca agcatagttg gagaaaacag atagaagacc aaatgaccag      3240
gctatgttct ccgagttgcc actctgtctc cgtcaaatgg cagcaactca atccagatgc      3300
gcccgaggcc ctgcaggccc cagcccaggt gccatccttg tttcgcaatg atcgactcct      3360
tgtctatgga ttcattcctc actgcacaca ggcaactctg tgtgcactaa ttcaagagaa      3420
agaattttgt acaatggtgt cgactactga gcttcagaag acaactggaa ctatgatcca      3480
caagctggca gcccgagctc taatcagaga ttatgaagat ggcattcttc acgaaaatga      3540
aaccagtcat gagatgaaaa aacaaacctt gaaatctctg attattaaac tcagtaaaga      3600
aaactctctc ataacacaat ttacaagctt tgtggcagtt gagaaaaggg atgagaatga      3660
gtcacctttt cctgatattc caaaagtttc tgaacttatt gccaaagaag atgtagactt      3720
cctgccctac atgagctggc agggggaacc ccaagaagcc gtcaggaacc agtctctttt      3780
agcatcctct gagtggccag aattacgttt atccaaacga aaacatagga aaattccatt      3840
ttccaaaaga aaaatggaat tatctcagcc agaagtttct gaagattttg aagaggatgc      3900
cttaggtgta ctaccagctt tcacatcaaa tttggaacgt ggacgtgtgg aaaagctatt      3960
ggatttaagt tggacagagt catgtaaacc aacagcaact gaaccactat ttaagaaagt      4020
cagtccatgg gaaacatcta cttctagctt ttttcctatt ttggctccgg ccgttggttc      4080
ctatcttacc ccgactaccc gcgctcacag tcctgcttcc ttgtcttttg cctcatatcg      4140
tcaggtagct agtttcggtt cagctgctcc tcccagacag tttgatgcat ctcaattcag      4200
ccaaggccct gtgcctggca cttgtgctga ctggatccca cagtcggcgt cttgtcccac      4260
aggacctccc cagaacccac cttctgcacc ctattgtggc attgtttttt cagggagctc      4320
attaagctct gcacagtctg ctccactgca acatcctgga ggctttacta ccaggccttc      4380
tgctggcacc ttccctgagc tggattctcc ccagcttcat ttctctcttc ctacagaccc      4440
tgatcccatc agaggttttg ggtcttatca tccctctgct tactctcctt ttcattttca      4500
accttccgca gcctctttga ctgccaacct taggctgcca atggcctctg ctttacctga      4560
ggctctttgc agtcagtccc ggactacccc agtagatctc tgtcttctag aagaatcagt      4620
aggcagtctc gaaggaagtc gatgtcctgt ctttgctttt caaagttctg acacagaaag      4680
tgatgagcta tcagaagtac ttcaagacag ctgcttttta caaataaaat gtgatacaaa      4740
agatgacagt atcccgtgct ttctggaagt aaaagaagag gatgaaatag tgtgcacaca      4800
acactggcag gatgctgtgc cttggacaga actcctcagt ctacagacag aggatggctt      4860
ctggaaactt acaccagaac tgggacttat attaaatctt aatacaaatg gtttgcacag      4920 cttctcttaaa caaaaaggca ttcaatctct aggtgtaaaa ggaagagaat gtctcctgga      4980
cctaattgcc acaatgctgg tactacagtt tattcgcacc aggttggaaa agagggaat       5040 agtgttcaaa tcactgatga aaatggatga cccttctatt tccaggaata ttccctgggc      5100
ttttgaggca ataaagcaag caagtgaatg ggtaagaaga actgaaggac agtacccatc      5160
tatctgccca cggcttgaac tggggaacga ctgggactct gccaccaagc agttgctggg      5220
actccagccc ataagcactg tgtcccctct tcatagagtc ctccattaca gtcaaggcta      5280
agtcaaatga aactgaattt taaacttttt gcatgcttct atgtagaaaa taatcaaatg      5340
ataatagata cttataatga aacttcatta aggtttcatt cagtgtagca attactgtct      5400
ttaaaaatta agtggaagaa gaattacttt aatcaactaa caagcaataa taaaatgaaa      5460
cttaaaat                                                              5468
```

<210> SEQ ID NO 2
<211> LENGTH: 1910
<212> TYPE: DNA
<213> ORGANISM: Homo sapiens

<400> SEQUENCE: 2

| | | | | | |
|---|---|---|---|---|---|
| ctagaattca | gcggccgctg | aattctaggc | ggcgcggcgg | cgacggagca | ccggcggcgg | 60 |
| cagggcgaga | gcattaaatg | aaagcaaaag | agttaataat | ggcaacacgg | ctccagaaga | 120 |
| ctcttcccct | gccaagaaaa | ctcgtagatg | ccagagacag | gagtcgaaaa | agatgcctgt | 180 |
| ggctggagga | aaagctaata | aggacaggac | agaagacaag | caagatggta | tgccaggaag | 240 |
| gtcatgggcc | agcaaaaggg | tctctgaatc | tgtgaaggcc | ttgctgttaa | agggcaaagc | 300 |
| tcctgtggac | ccagagtgta | cagccaaggt | ggggaaggtc | catgtgtatt | gtgaaggaaa | 360 |
| tgatgtctat | gatgtcatgc | taaatcagac | caatctccag | ttcaacaaca | acaagtacta | 420 |
| tctgattcag | ctattagaag | atgatgccca | gaggaacttc | agtgtttgga | tgagatgggg | 480 |
| ccgagttggg | aaaatgggac | agcacagcct | ggtggcttgt | tcaggcaatc | tcaacaaggc | 540 |
| caaggaaatc | tttcagaaga | aattccttga | caaaacgaaa | aacaattggg | aagatcgaga | 600 |
| aaagtttgag | aaggtgcctg | aaaatatgaa | tatgctacag | atggactatg | ccaccaatac | 660 |
| tcaggatgaa | gaggaaacaa | aaaagagga | atctcttaaa | tctcccttga | agccagagtc | 720 |
| acagctagat | cttcgggtac | aggagttaat | aaagttgatc | tgtaatgttc | aggccatgga | 780 |
| agaaatgatg | atggaaatga | agtataaatac | caagaaagcc | ccacttggga | agctgacagt | 840 |
| ggcacaaatc | aaggcaggtt | accagtctct | taagaagatt | gaggattgta | ttcgggctgg | 900 |
| ccagcatgga | cgagctctca | tggaagcatg | caatgaattc | tacaccagga | ttccgcatga | 960 |
| ctttggactc | cgtactcctc | cactaatccg | gacacagaag | gaactgtcag | aaaaaataca | 1020 |
| attactagag | gctttgggag | acattgaaat | tgctattaag | ctggtgaaaa | cagagctaca | 1080 |
| aagcccagaa | cacccattgg | accaacacta | tagaaaccta | cattgtgcct | tgcgcccct | 1140 |
| tgaccatgaa | agttacgagt | tcaaagtgat | ttcccagtac | ctacaatcta | cccatgctcc | 1200 |
| cacacacagc | gactatacca | tgaccttgct | ggatttgttt | gaagtggaga | aggatggtga | 1260 |
| gaaagaagcc | ttcagagagg | accttcataa | caggatgctt | ctatggcatg | gttccaggat | 1320 |
| gagtaactgg | gtgggaatct | tgagccatgg | gcttcgaatt | gcccaccctg | aagctcccat | 1380 |
| cacaggttac | atgtttggga | aaggaatcta | ctttgctgac | atgtcttcca | agagtgccaa | 1440 |
| ttactgcttt | gcctctcgcc | taaagaatac | aggactgctg | ctcttatcag | aggtagctct | 1500 |
| aggtcagtgt | aatgaactac | tagaggccaa | tcctaaggcc | gaaggattgc | ttcaaggtaa | 1560 |
| acatagcacc | aaggggctgg | gcaagatggc | tcccagttct | gcccacttcg | tcaccctgaa | 1620 |
| tgggagtaca | gtgccattag | gaccagcaag | tgacacagga | attctgaatc | cagatggtta | 1680 |
| taccctcaac | tacaatgaat | atattgtata | taaccccaac | caggtccgta | tgcggtacct | 1740 |
| tttaaaggtt | cagtttaatt | tccttcagct | gtggtgaatg | ttgatcttaa | ataaaccaga | 1800 |
| gatctgatct | tcaagcaaga | aaataagcag | tgttgtactt | gtgaattttg | tgatattta | 1860 |
| tgtaataaaa | actgtacagg | tctaaaaaaa | aaaaaaaaa | aaaaaaaaa | | 1910 |

<210> SEQ ID NO 3
<211> LENGTH: 2263
<212> TYPE: DNA
<213> ORGANISM: Homo sapiens

<400> SEQUENCE: 3

-continued

| | |
|---|---|
| tgggactggt cgcctgactc ggcctgcccc agcctctgct tcaccccact ggtggccaaa | 60 |
| tagccgatgt ctaatccccc acacaagctc atccccggcc tctgggattg ttgggaattc | 120 |
| tctccctaat tcacgcctga ggctcatgga gagttgctag acctgggact gccctgggag | 180 |
| gcgcacacaa ccaggccggg tggcagccag gacctctccc atgtccctgc ttttcttggc | 240 |
| catggctcca aagccgaagc cctgggtaca gactgagggc cctgagaaga agaagggccg | 300 |
| gcaggcagga agggaggagg acccctttccg ctccaccgct gaggccctca aggccatacc | 360 |
| cgcagagaag cgcataatcc gcgtggatcc aacatgtcca ctcagcagca accccgggac | 420 |
| ccaggtgtat gaggactaca actgcaccct gaaccagacc aacatcgaga caacaacaa | 480 |
| caagttctac atcatccagc tgctccaaga cagcaaccgc ttcttcacct gctggaaccg | 540 |
| ctggggccgt gtgggagagg tcggccagtc aaagatcaac cacttcacaa ggctagaaga | 600 |
| tgcaaagaag gactttgaga agaaatttcg ggaaaagacc aagaacaact gggcagagcg | 660 |
| ggaccacttt gtgtctcacc cgggcaagta cacacttatc gaagtacagg cagaggatga | 720 |
| ggcccaggaa gctgtggtga aggtggacag aggcccagtg aggactgtga ctaagcgggt | 780 |
| gcagccctgc tccctggacc cagccacgca gaagctcatc actaacatct tcagcaagga | 840 |
| gatgttcaag aacaccatgg ccctcatgga cctggatgtg aagaagatgc ccctgggaaa | 900 |
| gctgagcaag caacagattg cacggggttt cgaggccttg gaggcgctgg aggaggccct | 960 |
| gaaaggcccc acggatggtg gccaaagcct ggaggagctg tcctcacact tttacaccgt | 1020 |
| catcccgcac aacttcggcc acagccagcc cccgcccatc aattcccctg agcttctgca | 1080 |
| ggccaagaag gacatgctgc tggtgctggc ggacatcgag ctggcccagg ccctgcaggc | 1140 |
| agtctctgag caggagaaga cggtggagga ggtgccacac cccctggacc gagactacca | 1200 |
| gcttctcaag tgccagctgc agctgctaga ctctggagca cctgagtaca aggtgataca | 1260 |
| gacctactta gaacagactg gcagcaacca caggtgccct acacttcaac acatctggaa | 1320 |
| agtaaaccaa gaaggggagg aagacagatt ccaggcccac tccaaactgg gtaatcggaa | 1380 |
| gctgctgtgg catggcacca acatggccgt ggtggccgcc atcctcacta gtgggctccg | 1440 |
| catcatgcca cattctggtg ggcgtgttgg caagggcatc tactttgcct cagagaacag | 1500 |
| caagtcagct ggatatgtta ttggcatgaa gtgtggggcc caccatgtcg gctacatgtt | 1560 |
| cctgggtgag gtggccctgg gcagagagca ccatatcaac acggacaacc ccagcttgaa | 1620 |
| gagcccacct cctggcttcg acagtgtcat tgcccgaggc cacaccgagc ctgatccgac | 1680 |
| ccaggacact gagttggagc tggatggcca gcaagtggtg gtgccccagg ccagcctgt | 1740 |
| gccctgccca gagttcagca gctccacatt ctcccagagc gagtacctca tctaccagga | 1800 |
| gagccagtgt cgcctgcgct acctgctgga ggtccacctc tgagtgcccg ccctgtcccc | 1860 |
| cggggtcctg caaggctgga ctgtgatctt caatcatcct gcccatctct ggtaccccta | 1920 |
| tatcactcct ttttttcaag aatacaatac gttgttgtta actatagtca ccatgctgta | 1980 |
| caagatccct gaacttatgc ctcctaactg aaatttgtat tctttgaca catctgccca | 2040 |
| gtccctctcc tccagcccca tggtaaccag catttgactc tttacttgta tagggcagc | 2100 |
| ttttataggt tccacatgta agtgagatca tgcagtgttt gtctttctgt gcctggctta | 2160 |
| tttcactcag cataatgtgc accgggttca cccatgtttt cataaatgac aagatttcct | 2220 |
| cctttaaaaa aaaaaaaaaa aaaaaaaaaa aaaaaaaaaa aaa | 2263 |

<210> SEQ ID NO 4
<211> LENGTH: 4491

<212> TYPE: DNA
<213> ORGANISM: Homo sapiens

<400> SEQUENCE: 4

```
cgaagatggc ggcgtcgcgt cgctctcagc atcatcacca ccatcatcaa caacagctcc      60
agcccgcccc aggggcttca gcgccgccgc cgccacctcc tccccactc agccctggcc     120
tggccccggg gaccacccca gcctctccca cggccagcgg cctggccccc ttcgcctccc     180
cgcggcacgg cctagcgctg ccggaggggg atggcagtcg ggatccgccc gacaggcccc     240
gatccccgga cccggttgac ggtaccagct gttgcagtac caccagcaca atctgtaccg     300
tcgccgccgc tcccgtggtc ccagcggttt ctacttcatc tgccgctggg gtcgctccca     360
acccagccgg cagtggcagt aacaattcac cgtcgtcctc ttcttcccg acttcttcct     420
catcttcctc tccatcctcc cctggatcga gcttggcgga gagccccgag gcggccggag     480
ttagcagcac agcaccactg gggcctgggg cagcaggacc tgggacaggg gtcccagcag     540
tgagcgggc cctacgggaa ctgctggagg cctgtcgcaa tggggacgtg tcccgggtaa     600
agaggctggt ggacgcggca aacgtaaatg caaaggacat ggccggccgg aagtcttctc     660
ccctgcactt cgctgcaggt tttggaagga aggatgttgt agaacactta ctacagatgg     720
gtgctaatgt ccacgctcgt gatgatggag gtctcatccc gcttcataat gcctgttctt     780
ttggccatgc tgaggttgtg agtctgttat tgtgccaagg agctgatcca aatgccaggg     840
ataactggaa ctatacacct ctgcatgaag ctgctattaa agggaagatc gatgtgtgca     900
ttgtgctgct gcagcacgga gctgacccaa acattcggaa cactgatggg aaatcagccc     960
tggacctggc agatccttca gcaaaagctg tccttacagg tgaatacaag aaagacgaac    1020
tcctagaagc tgctaggagt ggtaatgaag aaaaactaat ggctttactg actcctctaa    1080
atgtgaattg ccatgcaagt gatgggcgaa agtcgactcc tttacatcta gcagcgggct    1140
acaacagagt tcgaatagtt cagcttcttc ttcagcatgg tgctgatgtt catgcaaaag    1200
acaaaggtgg acttgtgcct cttcataatg catgttcata tggacattat gaagtcacag    1260
aactgctact aaagcatgga gcttgtgtta atgccatgga tctctggcag tttactccac    1320
tgcacgaggc tgcttccaag aaccgtgtag aagtctgctc tttgttactt agccatggcg    1380
ctgatcctac gttagtcaac tgccatggca aaagtgctgt ggatatggct ccaactccgg    1440
agcttaggga gagattgact tatgaattta aggtcattc tttactacaa gcagccagag    1500
aagcagactt agctaaagtt aaaaaaacac tcgctctgga aatcattaat ttcaaacaac    1560
cgcagtctca tgaaacagca ctgcactgtg ctgtggcctc tctgcatccc aaacgtaaac    1620
aagtgacaga attgttactt agaaaaggag caaatgttaa tgaaaaaaat aaagatttca    1680
tgactcccct gcatgttgca gccgaaagag cccataatga tgtcatggaa gttctgcata    1740
agcatggcgc caagatgaat gcactggaca cccttggtca gactgctttg catagagccg    1800
ccctagcagg ccacctgcag acctgccgcc tcctgctgag ttacggctct gaccccctcca    1860
tcatctcctt acaaggcttc acagcagcac agatgggcaa tgaagcagtg cagcagattc    1920
tgagtgtgag ttacggctct gacccctcca tcatctcctt acaaggcttc acagcagcac    1980
agatgggcaa tgaagcagtg cagcagattc tgagtggtca ttcgtagata gtgatcattc    2040
tacttcagcc ttaatggtga tcttgagacg ggaagattta gaaggaaatc tatccagcat    2100
gtcttcactg tcaacatgaa gagtacacct atacgtactt ctgatgttga ttatcgactc    2160
ttagaggcat ctaaagctgg agacttggaa actgtgaagc aactttgcag ctctcaaaat    2220
```

```
gtgaattgta gagacttaga gggccggcat tccacgccct tacacttcgc agcaggctac    2280
aacagagtac acctatacgt acttctgatg ttgattatcg actcttagag gcatctaaag    2340
ctggagactt ggaaactgtg aagcaacttt gcagctctca aaatgtgaat tgtagagact    2400
tagagggccg gcattccacg cccttacact tcgcagcagg ctacaaccgc gtgtctgttg    2460
tagagtacct gctacaccac ggtgccgatg tccatgccaa agacaagggt ggcttggtgc    2520
cccttcataa tgcctgttca tatggacact atgaggtggc tgagctttta gtaaggcatg    2580
gggcttctgt caatgtggcg gacttatgga aatttacccc tctccatgaa gcagcagcta    2640
aaggaaagta tgaaatctgc aagctccttt taaaacatgg agcagatcca actaaaaaga    2700
acagagatgg aaatacacct ttggatttgg taaaggaagg agacacagat attcaggact    2760
tactgaaagg ggatgctgct tgttggatg ctgccaagaa gggctgcctg caagagtgc    2820
```

<210> TYPE: DNA
<213> ORGANISM: Homo sapiens

<400> SEQUENCE: 5

```
cgcgccgcct cgctagccga aacctgccca gccggtgccc ggccactgcg cacgcgcggg      60
acgacgtcac gtgcgctccc ggggctggac ggagctggca ggaggggcct tgccagcttc     120
cgccgccgcg tcgtttcagg acccggacgg cggattcgcg ctgcctccgc cgccgcgggg     180
cagccggggg gcagggagcc cagcgagggg cgcgcgtggg cgcggccatg ggactgcgcc     240
ggatccggtg acagcaggga gccaagcggc ccgggccctg agcgcgtctt ctccgggggg     300
cctcgccctc ctgctcgcgg ggccggggct cctgctccgg ttgctggcgc tgttgctggc     360
tgtggcggcg gccaggatca tgtcgggtcg ccgctgcgcc ggcgggggag cggcctgcgc     420
gagcgccgcg gccgaggccg tggagccggc cgcccgagag ctgttcgagg cgtgccgcaa     480
cggggacgtg gaacgagtca agaggctggt gacgcctgag aaggtgaaca gccgcgacac     540
ggcgggcagg aaatccaccc cgctgcactt cgccgcaggt tttgggcgga agacgtagt     600
tgaatatttg cttcagaatg gtgcaaatgt ccaagcacgt gatgatgggg gccttattcc     660
tcttcataat gcatgctctt ttggtcatgc tgaagtagtc aatctccttt tgcgacatgg     720
tgcagacccc aatgctcgag ataattggaa ttatactcct ctccatgaag ctgcaattaa     780
aggaaagatt gatgtttgca ttgtgctgtt acagcatgga gctgagccaa ccatccgaaa     840
tacagatgga aggacagcat tggatttagc agatccatct gccaaagcag tgcttactgg     900
tgaatataag aaagatgaac tcttagaaag tgccaggagt ggcaatgaag aaaaaatgat     960
ggctctactc acaccattaa atgtcaactg ccacgcaagt gatggcagaa agtcaactcc    1020
attacatttg gcagcaggat ataacagagt aaagattgta cagctgttac tgcaacatgg    1080
agctgatgtc catgctaaag ataaaggtga tctggtacca ttacacaatg cctgttctta    1140
tggtcattat gaagtaactg aacttttggt caagcatggt gcctgtgtaa atgcaatgga    1200
cttgtggcaa ttcactcctc ttcatgaggc agcttctaag aacaggggtg aagtatgttc    1260
tcttctctta agttatggtg cagacccaac actgctcaat tgtcacaata aaagtgctat    1320
agacttggct cccacaccac agttaaaaga aagattagca tatgaattta aaggccactc    1380
gttgctgcaa gctgcacgag aagctgatgt tactcgaatc aaaaaacatc tctctctgga    1440
aatggtgaat ttcaagcatc ctcaaacaca tgaaacagca ttgcattgtg ctgctgcatc    1500
tccatatccc aaaagaaagc aaatatgtga actgttgcta agaaaggag caaacatcaa    1560
tgaaaagact aaagaattct tgactcctct gcacgtggca tctgagaaag ctcataatga    1620
tgttgttgaa gtagtggtga acatgaagc aaaggttaat gctctggata atcttggtca    1680
gacttctcta cacagagctg catattgtgg tcatctacaa acctgccgcc tactcctgag    1740
ctatgggtgt gatcctaaca ttatatccct tcagggcttt actgctttac agatgggaaa    1800
tgaaaatgta cagcaactcc tccaagaggg tatctcatta ggtaattcag aggcagacag    1860
acaattgctg gaagctgcaa aggctggaga tgtcgaaact gtaaaaaaac tgtgtactgt    1920
tcagagtgtc aactgcagag acattgaagg gcgtcagtct acaccacttc attttgcagc    1980
tgggtataac agagtgtccg tggtggaata tctgctacag catggagctg atgtgcatgc    2040
taaagataaa ggaggccttg tacctttgca caatgcatgt tcttatggac attatgaagt    2100
tgcagaactt cttgttaaac atggagcagt agttaatgta gctgatttat ggaaatttac    2160
acctttacat gaagcagcag caaaaggaaa atatgaaatt tgcaaacttc tgctccagca    2220
```

```
tggtgcagac cctacaaaaa aaaacaggga tggaaatact cctttggatc ttgttaaaga    2280
tggagataca gatattcaag atctgcttag gggagatgca gctttgctag atgctgccaa    2340
gaagggttgt ttagccagag tgaagaagtt gtcttctcct gataatgtaa attgccgcga    2400
tacccaaggc agacattcaa cacctttaca tttagcagct ggttataata atttagaagt    2460
tgcagagtat ttgttacaac acggagctga tgtgaatgcc caagacaaag gaggacttat    2520
tcctttacat aatgcagcat cttacgggca tgtagatgta gcagctctac taataaagta    2580
taatgcatgt gtcaatgcca cggacaaatg gctttcaca cctttgcacg aagcagccca     2640
aaagggacga acacagcttt gtgctttgtt gctagcccat ggagctgacc cgactcttaa    2700
aaatcaggaa ggacaaacac ctttagattt agtttcagca gatgatgtca gcgctcttct    2760
gacagcagcc atgcccccat ctgctctgcc ctcttgttac aagcctcaag tgctcaatgg    2820
tgtgagaagc ccaggagcca ctgcagatgc tctctcttca ggtccatcta gcccatcaag    2880
cctttctgca gccagcagtc ttgacaactt atctgggagt ttttcagaac tgtcttcagt    2940
agttagttca agtggaacag agggtgcttc cagtttggag aaaaaggagg ttccaggagt    3000
agattttagc ataactcaat tcgtaaggaa tcttggactt gagcacctaa tggatatatt    3060
tgagagagaa cagatcactt tggatgtatt agttgagatg gggcacaagg agctgaagga    3120
gattggaatc aatgcttatg gacataggca caaactaatt aaaggagtcg agagacttat    3180
ctccggacaa caaggtctta acccatattt aactttgaac acctctggta gtggaacaat    3240
tcttatagat ctgtctcctg atgataaaga gtttcagtct gtggaggaag agatgcaaag    3300
tacagttcga gagcacagag atggaggtca tgcaggtgga atcttcaaca gatacaatat    3360
tctcaagatt cagaaggttt gtaacaagaa actatgggaa agatacactc accggagaaa    3420
agaagtttct gaagaaaacc acaaccatgc caatgaacga atgctatttc atgggtctcc    3480
ttttgtgaat gcaattatcc acaaaggctt tgatgaaagg catgcgtaca taggtggtat    3540
gtttggagct ggcatttatt ttgctgaaaa ctcttccaaa agcaatcaat atgtatatgg    3600
aattggagga ggtactgggt gtccagttca caaagacaga tcttgttaca tttgccacag    3660
gcagctgctc ttttgccggg taaccttggg aaagtctttc ctgcagttca gtgcaatgaa    3720
aatggcacat tctcctccag gtcatcactc agtcactggt aggcccagtg taaatggcct    3780
agcattagct gaatatgtta tttacagagg agaacaggct tatcctgagt atttaattac    3840
ttaccagatt atgaggcctg aaggtatggt cgatggataa atagttattt taagaaacta    3900
attccactga acctaaaatc atcaaagcag cagtggcctc tacgttttac tcctttgctg    3960
aaaaaaaatc atcttgccca caggcctgtg gcaaaaggat aaaaatgtga acgaagttta    4020
acattctgac ttgataaagc tttaataatg tacagtgttt tctaaatatt tcctgttttt    4080
tcagcacttt aacagatgcc attccaggtt aaactgggtt gtctgtacta aattataaac    4140
agagttaact tgaacctttt atatgttatg cattgattct aacaaactgt aatgccctca    4200
acagaactaa ttttactaat acaatactgt gttcttaaa acacagcatt tacactgaat     4260
acaatttcat ttgtaaaact gtaaataaga gcttttgtac tagcccagta tttatttaca    4320
ttgctttgta atataaatct gttttagaac tgcagcggtt tacaaaattt tttcatatgt    4380
attgttcatc tatacttcat cttacatcgt catgattgag tgatctttac atttgattcc    4440
agaggctatg ttcagttgtt agtgggaaa gattgagtta tcagatttaa tttgccgatg     4500 ggagcccttta tctgtcatta gaaatctttc tcatttaaga acttatgaat atgctgaaga   4560
tttaatttgt gataccttg tatgtatgag acacattcca aagagctcta actatgatag     4620
```

-continued

```
gtcctgatta ctaaagaagc ttctttactg gcctcaattt ctagctttca tgttggaaaa    4680
ttttctgcag tccttctgtg aaaattagag caaagtgctc ctgttttta gagaaactaa     4740 atcttgctgt tgaacaatta ttgtgttctt ttcatggaac ataagtagga tgttaacatt    4800
tccagggtgg aagggtaat cctaaatcat ttcccaatct attctaatta ccttaaatct     4860 aaagggaaa aaaaaatca caaacaggac tgggtagttt tttatcctaa gtatattttt      4920
tcctgttctt tttacttggt tttattgctg tatttatagc caatctatac atcatgggta    4980
aacttaaccc agaactataa aatgtagttg tttcagtccc cttcaggcct cctgaatggg    5040
caagtgcagt gaaacaggtg cttcctgctc ctgggttttc tctccatgat gttatgccca    5100
attggaaata tgctgtcagt ttgtgcacca tatggtgacc acgcctgtgc tcagtttggc    5160
agctatagaa ggaaatgctg tcccataaaa tgccatccct atttctaata taacactctt    5220
ttccaggaag catgcttaag catcttgtta cagagacata catccattat ggcttggcaa    5280 tctctttat ttgttgactc tagctccctt caaagtcgag aaagatctt tactcactta     5340 atgaggacat tccccatcac tgtctgtacc agttcacctt tatttacgt tttattcagt     5400 ctgtaaatta actggcccctt tgcagtaact tgtacataaa gtgctagaaa atcatgttcc   5460
ttgtcctgag taagagttaa tcagagtaag tgcatttctg gagttgtttc tgtgatgtaa    5520
attatgatca ttatttaaga agtcaaatcc tgatcttgaa gtgctttta tacagctctc     5580 taataattac aaatatccga aagtcatttc ttggaacaca agtggagtat gccaaatttt    5640
atatgaattt ttcagattat ctaagcttcc aggttttata attagaagat aatgagagaa    5700
ttaatggggt ttatatttac attatctctc aactatgtag cccatattac tcaccctatg    5760
agtgaatctg gaattgcttt tcatgtgaaa tcattgtggt ctatgagttt acaatactgc    5820
aaactgtgtt attttatcta aaccattgct taatgagtgt gttttccat gaatgaatat     5880 accgtggttc atatgttagc atggcagcat tttcagatag cttttttgttt gttgggaagt   5940 tggggttttg gggggagggg gagtattagt acgttgcatg gaatagccta ctttataatg    6000
atgggaatgc ttttctttt gttttgggat tttttttttt gaagtgaaat ttaacttttt     6060
gtgccagtag tactattata cccatcttca gtgtcttact tgtactgtat caaattccat    6120
accctcattt aattcttaat aaaactgttc acttgtaaaa aaaaaaaaa aaaaaaaaa      6180 aaaaaaaa                                                            6189
```

<210> SEQ ID NO 6
<211> LENGTH: 5489
<212> TYPE: DNA
<213> ORGANISM: Homo sapiens

<400> SEQUENCE: 6

```
cgcccgccca gccccggggg cagggaaagc ctaaattacg gaattaccgc gagcaaggag     60
cgcggaatcg gggagcgtcc ggagctagct ggatcctcta ggcaggatgg tgatgggaat    120
ctttgcaaat tgtatcttct gtttgaaagt gaagtactta cctcagcagc agaagaaaaa    180
gctacaaact gacattaagg aaaatggcgg aaagttttcc ttttcgttaa atcctcagtg    240
cacacatata atcttagata atgctgatgt tctgagtcag taccaactga attctatcca    300
aaagaaccac gttcatattg caaacccaga ttttatatgg aaatctatca gagaaaagag    360
actcttggat gtaaagaatt atgatcctta taagccctg gacatcacac cacctcctga    420
tcagaaggcg agcagttctg aagtgaaaac agaaggtcta tgcccggaca gtgccacaga    480
```

-continued

```
ggaggaagac actgtggaac tcactgagtt tggtatgcag aatgttgaaa ttcctcatct      540
tcctcaagat tttgaagttg caaaatataa caccttggag aaagtgggaa tggagggagg      600
ccaggaagct gtggtggtgg agcttcagtg ttcgcgggac tccagggact gtcctttcct      660
gatatcctca cacttcctcc tggatgatgg catggagact agaagacagt ttgctataaa      720
gaaaacctct gaagatgcaa gtgaatactt tgaaaattac attgaagaac tgaagaaaca      780
aggatttcta ctaagagaac atttcacacc tgaagcaacc caattagcat ctgaacaatt      840
gcaagcattg cttttggagg aagtcatgaa ttcaagcact ctgagccaag aggtgagcga      900
tttagtagag atgatttggg cagaggccct gggccacctg aacacatgc ttctcaagcc       960 agtgaacagg attagcctca cgatgtgag caaggcagag gggattctcc ttctagtaaa      1020
ggcagcactg aaaaatggag aaacagcaga gcaattgcaa aagatgatga cagagtttta     1080
cagactgata cctcacaaag gcacaatgcc caagaagtg aacctgggac tattggctaa      1140
gaaagcagac ctctgccagc taataagaga catggttaat gtctgtgaaa ctaatttgtc     1200
caaacccaac ccaccatccc tggccaaata ccgagctttg aggtgcaaaa ttgagcatgt     1260
tgaacagaat actgaagaat ttctcagggt tagaaaagag gttttgcaga atcatcacag     1320
taagagccca gtggatgtct tgcagatatt tagagttggc agagtgaatg aaaccacaga     1380 gttttttgagc aaacttggta atgtgaggcc cttgttgcat ggttctcctg tacaaaacat     1440
cgtgggaatc ttgtgtcgag ggttgctttt acccaaagta gtggaagatc gtggtgtgca     1500
aagaacagac gtcggaaacc ttggaagtgg gatttatttc agtgattcgc tcagtacaag     1560
tatcaagtac tcacacccgg gagagacaga tggcaccaga ctcctgctca tttgtgacgt     1620
agccctcgga aagtgtatgg acttacatga aaggactttt cccttaactg aagcaccacc     1680
aggctacgac agtgtgcatg gagtttcaca acagcctct gtcaccacag actttgagga     1740
tgatgaattt gttgtctata aaaccaatca ggttaaaatg aaatatatta ttaaattttc     1800
catgcctgga gatcagataa aggactttca tcctagtgat catactgaat tagaggaata     1860
cagacctgag ttttcaaatt tttcaaaggt tgaagattac cagttaccag atgccaaaac     1920
ttccagcagc accaaggccg gcctccagga tgcctctggg aacttggttc ctctggagga     1980
tgtccacatc aaagggagaa tcatagacac tgtagcccag gtcattgttt ttcagacata     2040
cacaaataaa agtcacgtgc ccattgaggc aaaatatatc tttcctttgg atgacaaggc     2100
cgctgtgtgt ggcttcgaag ccttcatcaa tgggaagcac atagttggag agattaaaga     2160
gaaggaagaa gcccagcaag agtacctaga agccgtgacc cagggccatg gcgcttacct     2220
gatgagtcag gatgctccgg acgttttac tgtaagtgtt ggaaacttac cccctaaggc      2280
taaggttctt ataaaaatta cctacatcac agaactcagc atcctgggca ctgttggtgt     2340
ctttttcatg cccgccaccg tagcaccctg gcaacaggac aaggctttga atgaaaacct     2400
tcaggataca gtagagaaga tttgtataaa agaaatagga acaaagcaaa gcttctcttt     2460
gactatgtct attgagatgc cgtatgtgat tgaattcatt ttcagtgata cacatgaact     2520
gaaacaaaag cgcacagact gcaaagctgt cattagcacc atggaaggca gctccttaga     2580
cagcagtgga ttttctctcc acatcggttt gtctgctgcc tatctcccaa gaatgtgggt     2640
gaaaaacatc cagaaaaaga aagcgaggct tgcatgcttg tctttcaacc cgatctcgat     2700
gtcgacctcc ctgacctagc cagtgagagc gaagtgatta tttgtcttga ctgctccagt     2760
tccatggagg gtgtgacatt cttgcaagcc aagcaaatca ccttgcatgc gctgtccttg     2820
gtgggtgaga agcagaaagt aaatattatc cagttcggca caggttacaa ggagctattt     2880
```

```
tcgtatccta agcatatcac aagcaatacc acggcagcag agttcatcat gtctgccaca    2940
cctaccatgg ggaacacaga cttctggaaa acactccgat atcttagctt attgtaccct    3000
gctcgagggt cacggaacat cctcctggtg tctgatgggc acctccagga tgagagcctg    3060
acattacagc tcgtgaagag gagccgcccg cacaccaggt tattcgcctg cggtatcggt    3120
tctacagcaa atcgtcacgt cttaaggatt ttgtcccagt gtggtgccgg agtatttgaa    3180
tattttaatg caaaatccaa gcatagttgg agaaaacaga tagaagacca aatgaccagg    3240
ctatgttctc cgagttgcca ctctgtctcc gtcaaatggc agcaactcaa tccagatgcg    3300
cccgaggccc tgcaggcccc agcccaggtg ccatccttgt ttcgcaatga tcgactcctt    3360
gtctatggat tcattcctca ctgcacacaa gcaactctgt gtgcactaat tcaagagaaa    3420
gaattttgta caatggtgtc gactactgag cttcagaaga caactggaac tatgatccac    3480
aagctggcag cccgagctct aatcagagat tatgaagatg gcattcttca cgaaaatgaa    3540
accagtcatg agatgaaaaa acaaaccttg aaatctctga ttattaaact cagtaaagaa    3600
aactctctca taacacaatt tacaagcttt gtggcagttg agaaaaggga tgagaatgag    3660
tcgccttttc ctgatattcc aaaagtttct gaacttattg ccaagaaga tgtagacttc    3720
ctgccctaca tgagctggca gggggagccc caagaagccg tcaggaacca gtctcttttta   3780
gcatcctctg agtggccaga attacgttta tccaaacgaa aacataggaa aattccattt    3840
tccaaaagaa aaatggaatt atctcagcca gaagtttctg aagattttga agaggatggc    3900
ttaggtgtac taccagcttt cacatcaaat ttggaacgtg gaggtgtgga aaagctattg    3960
gatttaagtt ggacagagtc atgtaaacca acagcaactg aaccactatt taagaaagtc    4020
agtccatggg aaacatctac ttctagcttt tttcctattt tggctccggc cgttggttcc    4080
tatcttaccc cgactacccg cgctcacagt cctgcttcct tgtcttttgc ctcatatcgt    4140
caggtagcta gtttcggttc agctgctcct cccagacagt ttgatgcatc tcaattcagc    4200
caaggccctg tgcctggcac ttgtgctgac tggatcccac agtcggcgtc ttgtcccaca    4260
ggacctcccc agaacccacc ttctgcaccc tattgtggca ttgttttttc agggagctca    4320
ttaagctctg cacagtctgc tccactgcaa catcctggag ctttactac caggccttct    4380
gctggcacct tccctgagct ggattctccc cagcttcatt tctctcttcc tacagaccct    4440
gatcccatca gaggttttgg gtcttatcat ccctctgctt actctccttt tcatttttcaa    4500
ccttccgcag cctctttgac tgccaacctt aggctgccaa tggcctctgc tttacctgag    4560
gctctttgca gtcagtcccg gactacccca gtagatctct gtcttctaga agaatcagta    4620
ggcagtctcg aaggaagtcg atgtcctgtc tttgcttttc aaagttctga cacagaaagt    4680
gatgagctat cagaagtact tcaagacagc tgcttttac aaataaagtg tgatacaaaa    4740
gatgacagta tcccgtgctt tctggaatta aagaagagg atgaaatagt gtgcacacaa    4800
cactggcagg atgctgtgcc ttggacagaa ctcctcagtc tacagacaga ggatggcttc    4860
tggaaactta caccagaact gggacttata ttaaatctta atacaaatgg tttgcacagc    4920
tttcttaaac aaaaaggcat tcaatctcta ggtgtaaaag aagagaatg tctcctggac    4980
ctaattgcca caatgctggt actacagttt attcgcacca ggttggaaaa agagggaata    5040
gtgttcaaat cactgatgaa aatggatgac ccttctattt ccaggaatat tccctgggct    5100
tttgaggcaa taaagcaagc aagtgaatgg gtaagaagaa ctgaaggaca gtacccatct    5160
atctgcccac ggcttgaact ggggaacgac tgggactctg ccaccaagca gttgctggga    5220
```

```
ctccagccca taagcactgt gtccctctt catagagtcc tccattacag tcaaggctaa    5280
gtcaaatgaa actgaatttt aaactttttg catgcttcta tgtagaaaat aatcaaatga    5340
taatagataa ttataatgaa acttcattaa ggtttcattc agtgtagcaa ttactgtctt    5400
taaaaattaa gtggaagaag aattacttta atcaactaac aagcaataat aaaatgaaac    5460
ttaaaataaa aaaaaaaaaa aaaaaaaaa                                      5489
```